(12) United States Patent
Ehrenreich et al.

(10) Patent No.: US 9,155,869 B2
(45) Date of Patent: Oct. 13, 2015

(54) CATHETER HAVING INFLATION AND DEFLATION LUMEN USEFUL FOR PREVENTING OR REDUCING REPERFUSION INJURY

(75) Inventors: Kevin J. Ehrenreich, San Francisco, CA (US); Jesus Magana, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 188 days.

(21) Appl. No.: 12/771,946

(22) Filed: Apr. 30, 2010

(65) Prior Publication Data

US 2011/0270176 A1 Nov. 3, 2011

(51) Int. Cl.
| | |
|---|---|
| A61M 29/00 | (2006.01) |
| A61M 25/10 | (2013.01) |
| A61M 39/10 | (2006.01) |
| A61M 39/22 | (2006.01) |
| A61M 25/00 | (2006.01) |

(52) U.S. Cl.
CPC .......... *A61M 25/1018* (2013.01); *A61M 39/105* (2013.01); *A61M 39/22* (2013.01); *A61M 25/1002* (2013.01); *A61M 2025/004* (2013.01); *A61M 2025/0059* (2013.01)

(58) Field of Classification Search
CPC ................ A61M 25/1018; A61M 25/10184; A61M 25/10187; A61M 2025/1052; A61M 2025/1061; A61M 2025/1071; A61M 2025/1079; A61M 2025/1095; A61M 2025/1097
USPC .......... 604/99.01–99.04, 100.01, 100.03, 104
See application file for complete search history.

(56) References Cited

U.S. PATENT DOCUMENTS

| | | | |
|---|---|---|---|
| 3,190,291 A | 6/1965 | Foley | |
| 3,378,011 A | 4/1968 | Vitello | |
| 3,860,007 A | 1/1975 | Binard | |
| 4,740,203 A | 4/1988 | Hoskins | |
| 4,861,520 A | 8/1989 | van't Hooft et al. | |
| 4,878,898 A | 11/1989 | Griffin et al. | |
| 5,011,468 A * | 4/1991 | Lundquist et al. | 600/18 |
| 5,059,167 A | 10/1991 | Lundquist et al. | |
| 5,085,249 A | 2/1992 | Dragan | |
| 5,336,184 A * | 8/1994 | Teirstein | 604/103.04 |
| 5,425,713 A * | 6/1995 | Taylor et al. | 604/100.03 |
| 5,484,411 A | 1/1996 | Inderbitzen et al. | |
| 5,500,013 A | 3/1996 | Buscemi et al. | |

(Continued)

FOREIGN PATENT DOCUMENTS

| | | |
|---|---|---|
| EP | 0376451 | 7/1990 |
| EP | 0710490 | 5/1996 |

(Continued)

OTHER PUBLICATIONS

ISR/WO for PCT/US2010/033276 dated Jul. 30, 2010.

(Continued)

*Primary Examiner* — Jason Flick
*Assistant Examiner* — Melissa A Snyder
(74) *Attorney, Agent, or Firm* — Randy Shen; Blakely Sokoloff Taylor & Zafman LLP

(57) ABSTRACT

A system including a catheter and an expandable member. The catheter includes an independent inflation lumen and an separate independent deflation lumen capable of sequential inflation and deflation of an expandable member in rapid succession, such as less than five seconds.

46 Claims, 33 Drawing Sheets

(56) References Cited

U.S. PATENT DOCUMENTS

| | | | |
|---|---|---|---|
| 5,695,468 A | 12/1997 | Lafontaine | |
| 5,728,064 A | 3/1998 | Burns et al. | |
| 5,749,852 A | 5/1998 | Schwab et al. | |
| 5,814,016 A | 9/1998 | Valley et al. | |
| 5,885,244 A * | 3/1999 | Leone et al. | 604/508 |
| 5,902,268 A * | 5/1999 | Saab | 604/96.01 |
| 5,925,054 A | 7/1999 | Taylor et al. | |
| 5,972,019 A | 10/1999 | Engelson et al. | |
| 5,976,119 A | 11/1999 | Spears et al. | |
| 6,071,305 A | 6/2000 | Brown et al. | |
| 6,295,990 B1 | 10/2001 | Lewis et al. | |
| 6,435,189 B1 | 8/2002 | Lewis et al. | |
| 6,436,087 B1 | 8/2002 | Lewis et al. | |
| 6,436,090 B1 | 8/2002 | Sanchez et al. | |
| 6,468,200 B1 | 10/2002 | Fischi | |
| 6,580,457 B1 | 6/2003 | Armstrong et al. | |
| 6,746,465 B2 | 6/2004 | Diederich et al. | |
| 6,767,345 B2 | 7/2004 | St. Germain et al. | |
| 6,900,008 B2 | 5/2005 | Vinten-Johansen et al. | |
| 6,902,268 B1 | 6/2005 | King et al. | |
| 6,986,880 B2 | 1/2006 | Coniglione et al. | |
| 7,166,097 B2 | 1/2007 | Barbut | |
| 7,195,610 B1 | 3/2007 | Flachbart | |
| 7,220,252 B2 | 5/2007 | Shah | |
| 7,335,192 B2 | 2/2008 | Keren et al. | |
| 7,364,566 B2 | 4/2008 | Elkins et al. | |
| 7,468,028 B2 | 12/2008 | Schneider et al. | |
| 7,468,070 B2 | 12/2008 | Henry et al. | |
| 7,500,982 B2 | 3/2009 | Pepper | |
| 7,674,240 B2 | 3/2010 | Webler et al. | |
| 7,686,781 B2 | 3/2010 | Vinten-Johansen | |
| 7,954,924 B2 | 6/2011 | Linliu | |
| 8,162,879 B2 * | 4/2012 | Hattangadi et al. | 604/101.03 |
| 8,221,348 B2 | 7/2012 | Hackett et al. | |
| 2002/0082548 A1 | 6/2002 | Sanchez et al. | |
| 2003/0014071 A1 | 1/2003 | Reynolds et al. | |
| 2003/0078538 A1 * | 4/2003 | Neale et al. | 604/98.01 |
| 2003/0100830 A1 | 5/2003 | Zhong et al. | |
| 2003/0199865 A1 | 10/2003 | Knudson et al. | |
| 2003/0199917 A1 | 10/2003 | Knudson et al. | |
| 2004/0111079 A1 | 6/2004 | Heyes et al. | |
| 2004/0243057 A1 | 12/2004 | Vinten-Johansen | |
| 2004/0255956 A1 | 12/2004 | Vinten-Johansen et al. | |
| 2005/0070848 A1 | 3/2005 | Kim et al. | |
| 2005/0118562 A1 | 6/2005 | Vinten-Johansen et al. | |
| 2006/0030814 A1 | 2/2006 | Valencia et al. | |
| 2006/0064059 A1 | 3/2006 | Gelfand et al. | |
| 2006/0079573 A1 | 4/2006 | Vinten-Johansen et al. | |
| 2006/0100639 A1 | 5/2006 | Levin et al. | |
| 2006/0189960 A1 | 8/2006 | Kesten et al. | |
| 2006/0205671 A1 | 9/2006 | Vinten-Johansen | |
| 2007/0010847 A1 * | 1/2007 | Pepper | 606/194 |
| 2007/0129752 A1 | 6/2007 | Webler et al. | |
| 2007/0142818 A1 * | 6/2007 | Webler et al. | 604/509 |
| 2007/0160645 A1 | 7/2007 | Vinten-Johansen | |
| 2008/0097383 A1 | 4/2008 | Vinten-Johansen | |
| 2008/0097385 A1 | 4/2008 | Vinten-Johansen et al. | |
| 2009/0018498 A1 | 1/2009 | Chiu et al. | |
| 2010/0082012 A1 * | 4/2010 | Hattangadi et al. | 604/509 |
| 2010/0099946 A1 * | 4/2010 | Jenkins et al. | 600/104 |
| 2010/0198249 A1 | 8/2010 | Sabliere | |
| 2010/0324429 A1 | 12/2010 | Leschinsky | |
| 2011/0224606 A1 | 9/2011 | Shome et al. | |

FOREIGN PATENT DOCUMENTS

| | | |
|---|---|---|
| EP | 1626764 B | 1/2010 |
| WO | WO 01/41861 | 6/2001 |
| WO | 0160443 | 8/2001 |
| WO | 02078535 | 10/2002 |
| WO | 2008117256 | 10/2008 |

OTHER PUBLICATIONS

ISR/WO for PCT/US2010/033270 dated Jul. 9, 2010.

Dirksen et al., "Reperfusion injury in humans: a review of clinical trials on reperfusion injury inhibitory strategies," Cardiovasc Res. Jun. 1, 2007;74(3):343-55. Epub Jan. 23, 2007.

Hanssen et al., "Heparin-releasing intravascular guidewires," Med Device Technol. Sep. 2002;13(7):20-2.

Jennings et al., "Preconditioning myocardium with ischemia," Cardiovascular Drugs and Therapy, vol. 5, No. 5, 933-938, DOI: 10.1007/BF00053555.

Kin et al., "Postconditioning attenuates myocardial ischemia—reperfusion injury by inhibiting events in the early minutes of reperfusion," Cardiovasc Res (2004) 62 (1): 74-85.

Murry et al., "Preconditioning with ischemia: a delay of lethal cell injury in ischemic myocardium," Circulation. 1986;74:1124-1136.

Peerlings et al., "Heparin release from slippery-when-wet guide wires for intravascular use," J Biomed Mater Res. 2002;63(6):692-8.

Piot et al., "Effect of Cyclosporine on Reperfusion Injury in Acute Myocardial Infarction," N Engl J Med. Jul. 31, 2008;359(5):473-8.

Staat et al., "Postconditioning the Human Heart," Circulation. 2005;112:2143-2148.

Tsang et al., "Postconditioning: A Form of "Modified Reperfusion" Protects the Myocardium by Activating the Phosphatidylinositol 3-Kinase-Akt Pathway," Circulation Research. 2004;95 :230-232.

Vasquez et al., "Myocardial protection with preconditioning," Circulation. 1990;82:609-619.

Yang et al., "Multiple, brief coronary occlusions during early reperfusion protect rabbit hearts by targeting cell signaling pathways," Journal of the American College of Cardiology, vol. 44, Issue 5, Sep. 1, 2004, pp. 1103-1110.

Yellon et al., "Myocardial reperfusion injury," N Engl J Med. Sep. 13, 2007;357(11):1121-35.

Zhao et al., "Inhibition of myocardial injury by ischemic postconditioning during reperfusion: comparison with ischemic preconditioning," AJP—Heart Aug. 2003 vol. 285 No. 2 H579-H588.

Poppenga et al., "Assessment of Potential Therapies for Acute T-2 Toxicosis in The Rat," 1987, Toxicon, vol. 25, No. 5, pp. 537-546, Department of Veterinary Biosciences, University of Illinois, Urbana, IL 61801, U.S.A.

Heng Zhao, "Ischemic Postconditioning as a Novel Avenue to Protect Against Brain Injury After Stroke" Journal of Cerebral Blood Flow & Metabolism (2009) 29, 873-885, Department of Neurosurgery, Stanford University School of Medicine, Stanford, California, U.S.A.

Jan. 5, 2012 Office Action issued in U.S. Appl. No. 12/771,946, filed Apr. 30, 2010.

Apr. 5, 2012 Applicant response to Jan. 5, 2012 Office Action issued in U.S. Appl. No. 12/771,946, filed Apr. 30, 2010.

Dec. 22, 2011 Office Action issued in U.S. Appl. No. 12/771,968, filed Apr. 30, 2010.

Mar. 22, 2012 Applicant response to Dec. 22, 2011 Office Action issued in U.S. Appl. No. 12/771,968, filed Apr. 30, 2010.

Jan. 5, 2012 Office Action issued in U.S. Appl. No. 13/098,134, filed Apr. 29, 2011.

Apr. 5, 2012 Applicant response to Jan. 5, 2012 Office Action issued in U.S. Appl. No. 13/098,134, filed Apr. 29, 2011.

Oct. 11, 2012 Office Action issued in U.S. Appl. No. 13/098,092, filed Apr. 29, 2011.

Dec. 28, 2012 Applicant response to Oct. 11, 2012 Office Action issued in U.S. Appl. No. 13/098,092, filed Apr. 29, 2011.

Oct. 9, 2012 Office Action issued in U.S. Appl. No. 13/098,055, filed Apr. 29, 2011.

Feb. 11, 2013 response to Oct. 9, 2012 Office Action issued in U.S. Appl. No. 13/098,055, filed Apr. 29, 2011.

Oct. 17, 2012 Office Action issued in U.S. Appl. No. 13/032,733, filed Feb. 23, 2011.

Feb. 12, 2013 response to Oct. 17, 2012 Office Action issued in U.S. Appl. No. 13/032,733, filed Feb. 23, 2011.

Zhi-Qing Zhao and Jakob Vinten-Johansen, Postconditioning: Reduction of reperfusion-induced injury. Cardiovasc Res (2006) 70(2): 200-211.

Communication from EPO, dated Jan. 29, 2014.

UKIPO Examination Report for GB1219332.2 dated Sep. 19, 2013.

UKIPO Examination Report for GB1315742.5 dated Sep. 19, 2013.

(56) References Cited

OTHER PUBLICATIONS

SIPO Search Report for Chinese patent application No. 201180028064.7.
SIPO Search Report in Chinese Application No. 201080067243.7.
Written Opinion and Search Report for PCT Application No. PCT/US2011/034621.
W. Shi and J. Vinten-Johansen, Endogenous cardioprotection by ischaemic postconditioning and remote conditioning, Cardiovascular Research (2012) 94, 206-216.
J. Vinten-Johansen and W. Shi, The science and clinical translation of remote postconditioning, J Cardiovasc Med, 2013, 14:206-213.

* cited by examiner

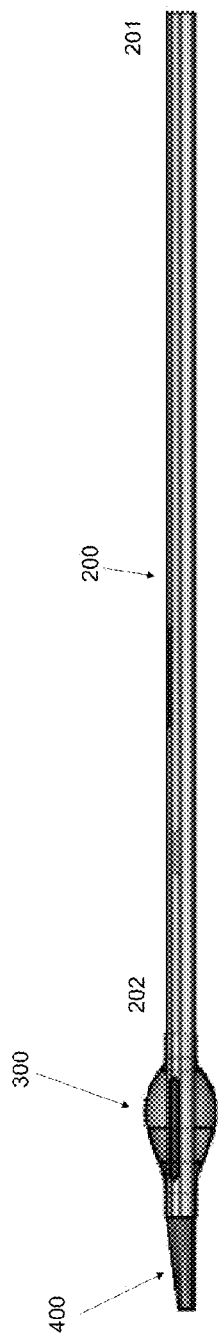
FIGURE 3A
FIGURE 3B
FIGURE 3C

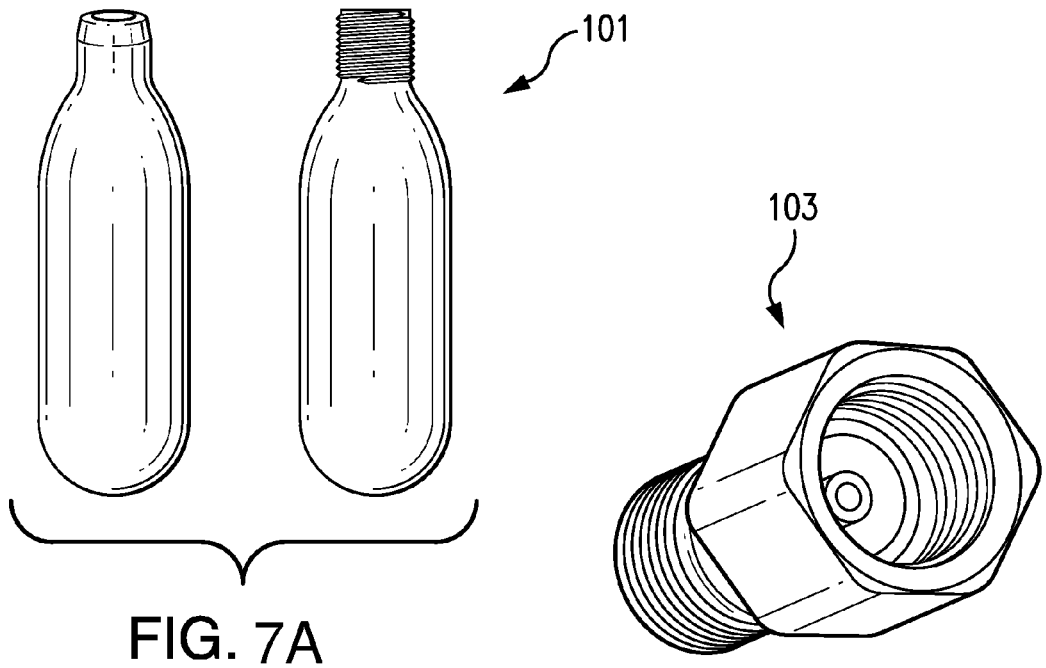
FIG. 7A
FIG. 7B
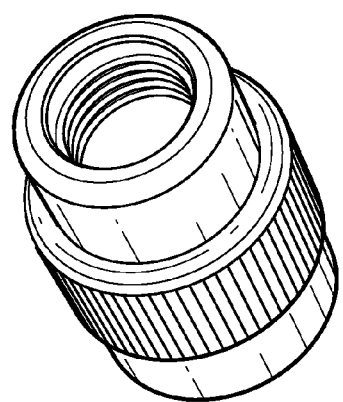
FIG. 7C
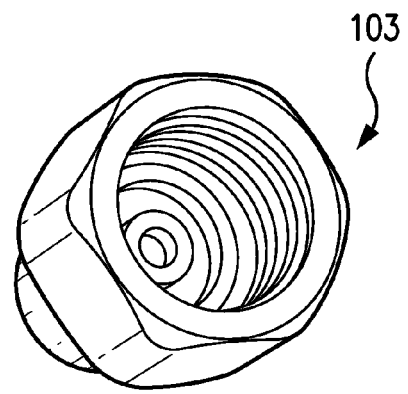
FIG. 7D 2.5 mm CHEK

INSTALLATION HOLE

ACTUAL SIZE

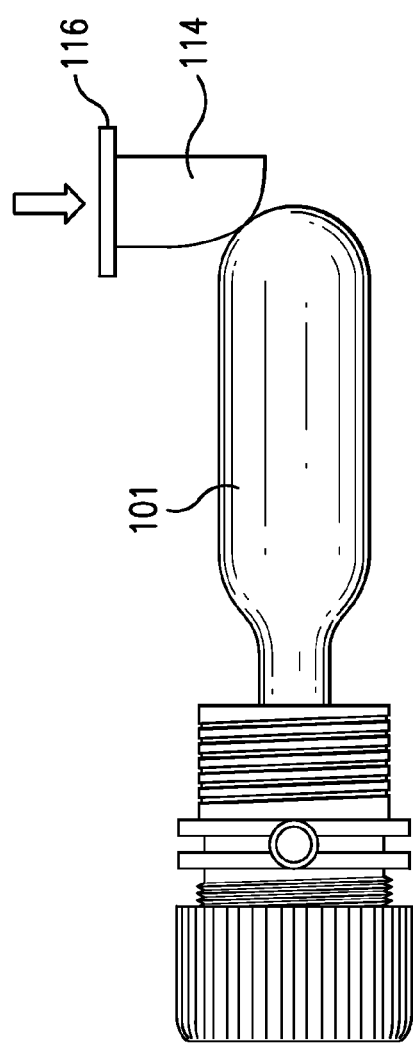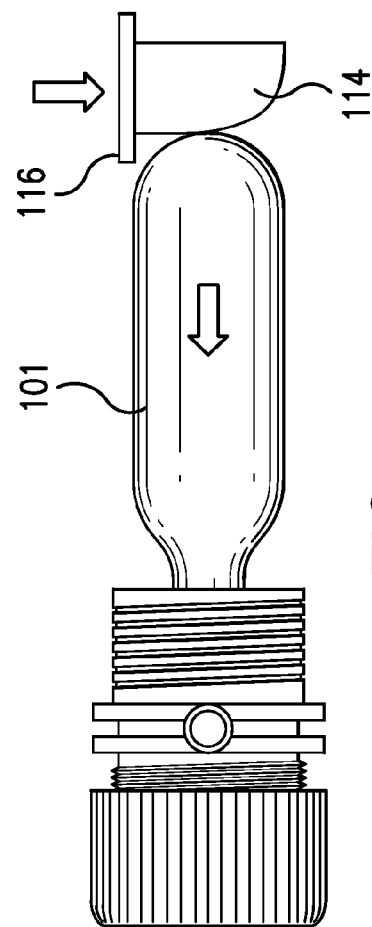

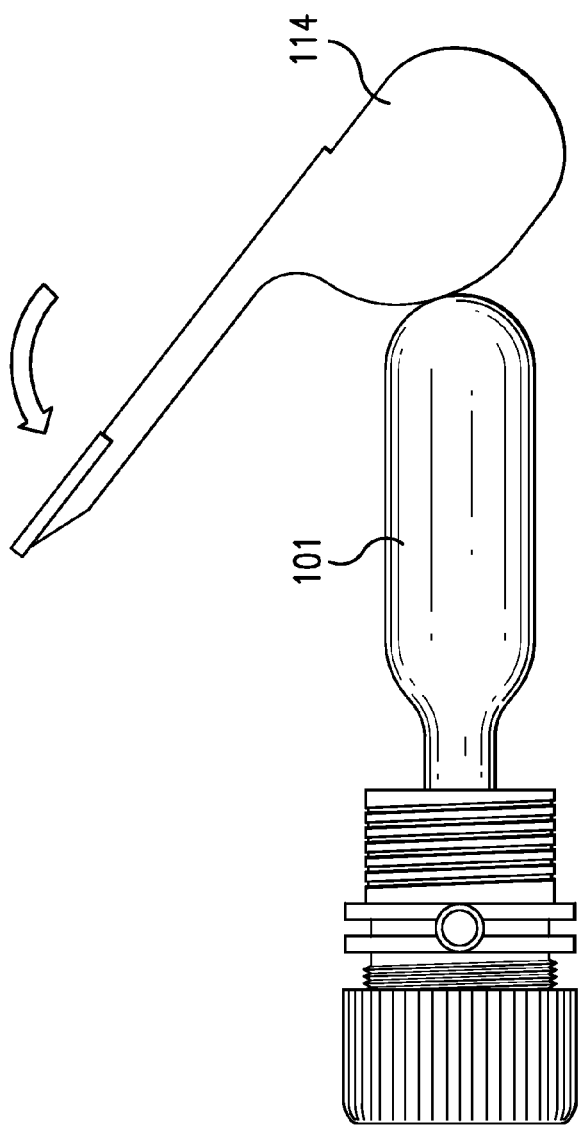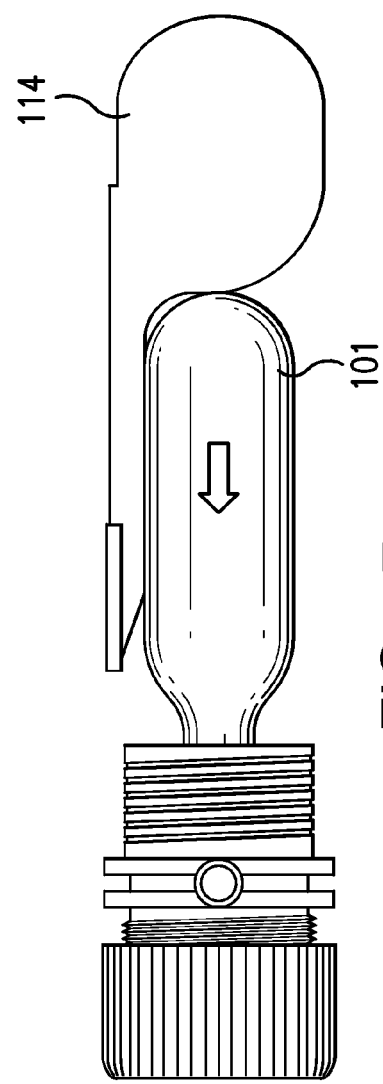

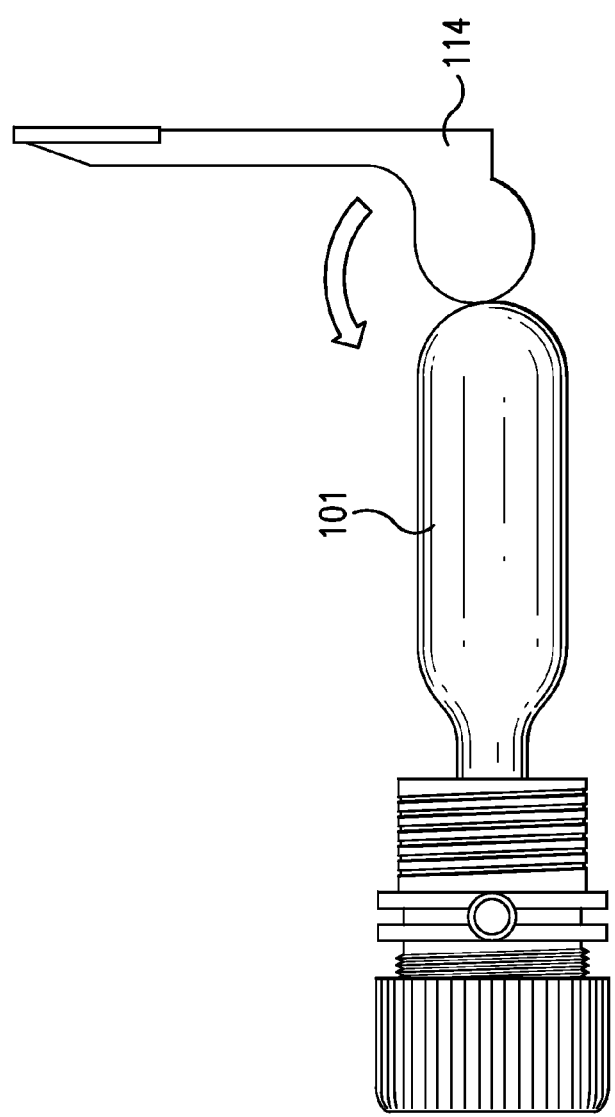
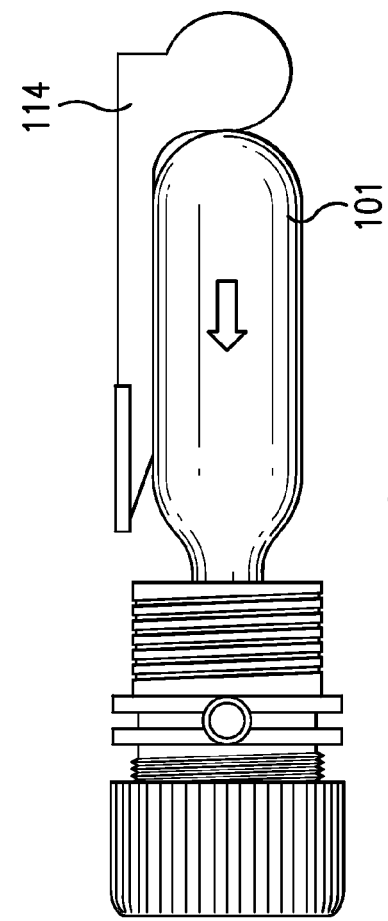

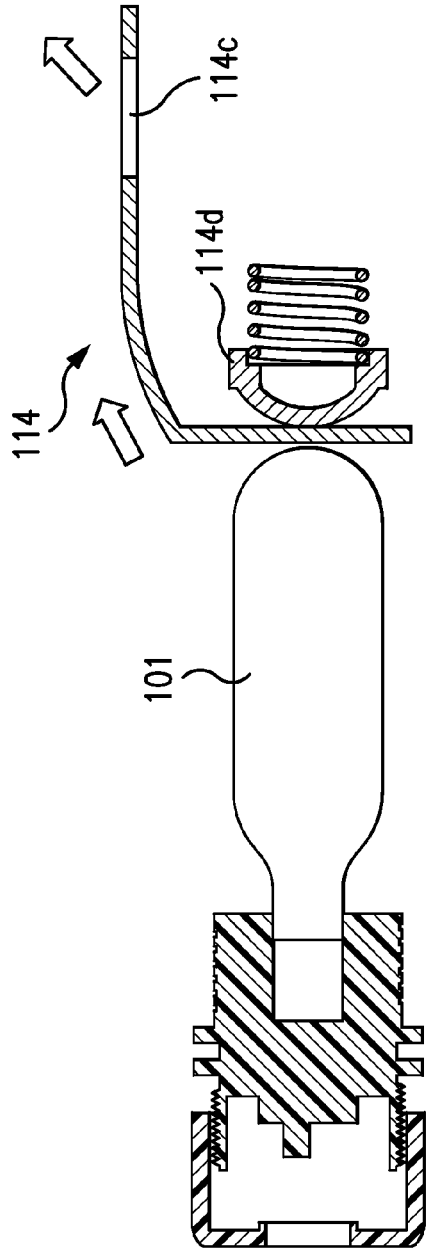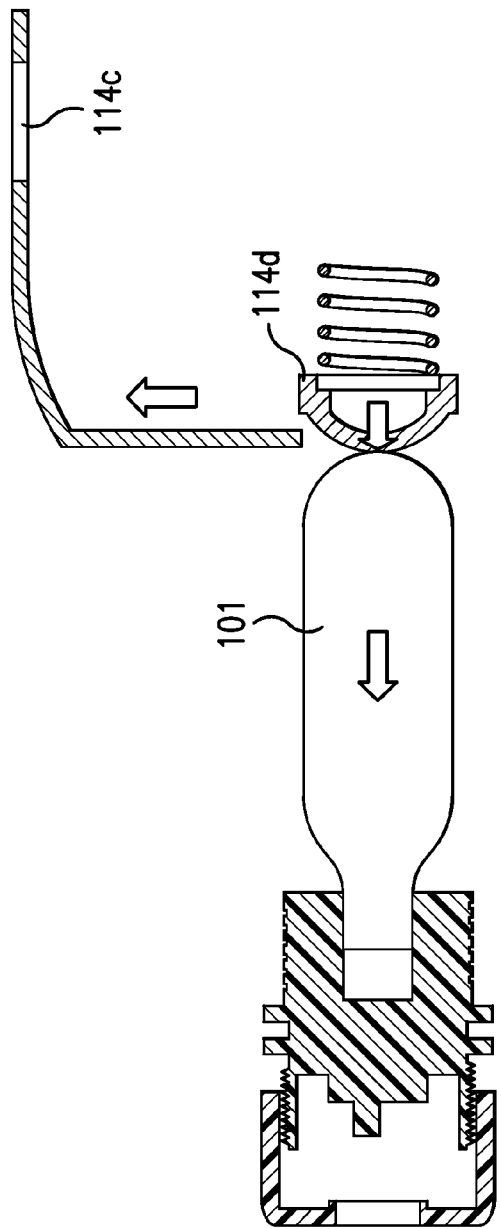

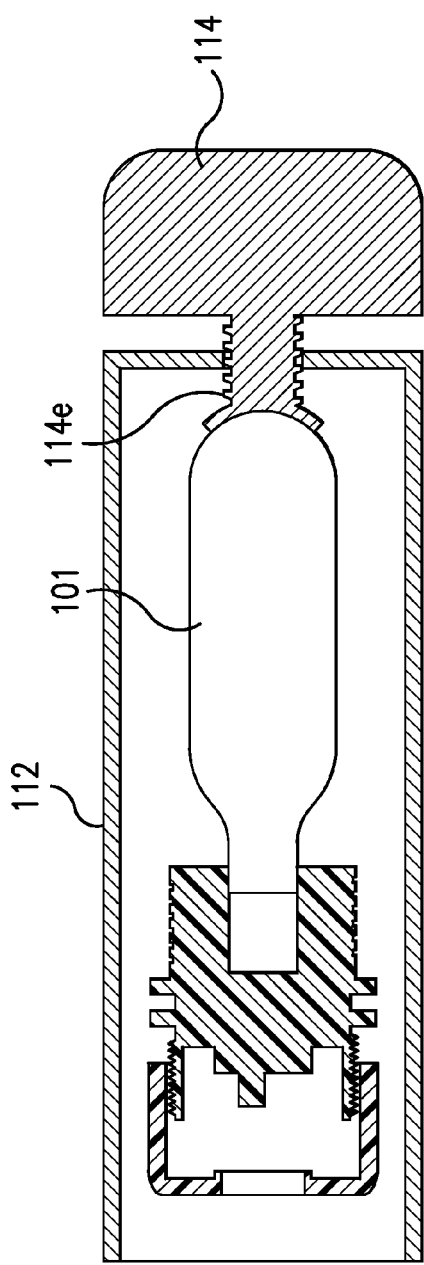
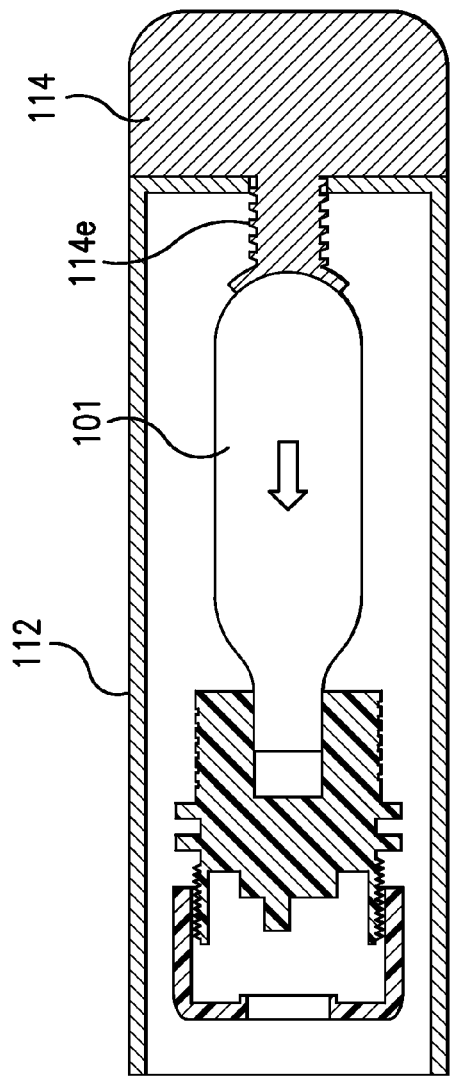
FIG. 9M
FIG. 9N

CATHETER HAVING INFLATION AND DEFLATION LUMEN USEFUL FOR PREVENTING OR REDUCING REPERFUSION INJURY

FIELD OF THE INVENTION

The invention relates to catheter systems. More particularly, the invention relates to a catheter having an inflation lumen and independent deflation lumen to permit rapid, sequential, inflation and deflation of an expandable member, such as a balloon, which is particularly useful in reducing the manifestation of reperfusion injury with post-conditioning techniques.

BACKGROUND OF THE INVENTION

When a patient suffers from an ischemic event in the coronary, peripheral or cerebral vasculature the blood supply to tissues and organs distal to the blockage or occlusion is significantly diminished. The resulting deprivation of oxygen increases the risk of necrosis of the tissues and organs. Generally, a patient suffering an ischemic event is treated by minimally invasive catheterization, such as for example percutaneous transluminal coronary angioplasty (PCTA) if the blockage occurs in the coronary vasculature. PCTA is employed to dilate the ischemic blockage and to restore the blood supply to the tissues and organs. Rapid restoration of blood flow after an ischemic event minimizes the duration of insufficient oxygenation to the tissue and organs, and therefore optimizes tissue and organ survival. However, it has now been found that restoring blood supply in a rapid and consistent manner results in reperfusion injury. A shock to the tissues and organs from rapid oxygen re-saturation and abrupt changes to pH level in the tissue can result in an overall increase in the infarct size.

Reperfusion injury results from the rapid opening of a blood vessel of the coronary, peripheral, and/or cerebral vasculature after a period of ischemia also known as reduced blood flow. For example, the rapid opening of an artery of the heart during a ST-Elevation Myocardial Infarction ("STEMI"), or an artery to the brain (ischemic stroke), or an artery to the other vital organs such as the kidney, liver or other tissues of the body sometimes causes ischemic injury in myocardial, cerebral, peripheral and spinal infarction, for example. One method to reduce or prevent the occurrence of reperfusion injury is a technique known as post-conditioning. Post-conditioning is a method during which the blood flow in the infarcted artery is stopped and started for multiple cycles immediately after re-opening of initial flow from the STEMI or other blockage. This re-opening of blood flow can be either before or after angioplasty, with or without placement of a stent.

Currently, physicians typically use a conventional angioplasty catheter to perform post-conditioning techniques. However, the use of an angioplasty catheter is not optimal for post-conditioning. For example, the angioplasty balloon is not configured to quickly occlude flow, nor is it configured to withstand multiple and sequential inflation and deflation cycles. Instead, the angioplasty balloon is designed to carefully create a new, circular lumen. Additionally, the typical angioplasty balloon is non-compliant, meaning it is designed and/or made of a material that is meant to be inflated with a range of pressures, while not significantly changing its outer diameter size. A typical non-compliant angioplasty balloon becomes circular at approximately 4 atmospheres of pressure. As the balloon pressure is increased, the outer diameter grows very little even as pressure is increased to 14-18 atmospheres. Such balloon characteristics can be drawbacks for post-conditioning. Further, an angioplasty balloon is typically designed to open a stenosis or blood vessel along a lesion, rather than just occlude flow. Thus, the length of an angioplasty balloon is generally between 8 mm to 40 mm, while an occlusion balloon could have a smaller length.

Another major drawback to using a conventional angioplasty catheter for post conditioning is efficiency. Prior to use the physician must measure the blood vessel, for example, by fluoroscopy, then size the balloon both for length and diameter, and then go through various steps to prepare the balloon such as removing the air trapped within the balloon before filling the balloon with saline/contrast mixture. Thus, using the angioplasty catheter with the angioplasty balloon suffers from inefficiencies. Further, the angioplasty catheter typically must be manually actuated to both inflate and deflate the balloon. For example, the use of an angioplasty catheter for post-conditioning usually requires rapid rotation of a screw piston in order to deliver the fluid in a controlled manner, while watching the pressure gage of an Indeflator. Inflation of the balloon to a circular size can require 10-20 twists of the Indeflator in order to expand the balloon. During deflation, the Indeflator is normally directly unlocked and rapidly deflated. If a controlled deflation is required, then the Indeflator can be manually screwed down to a lower pressure. Due to the extent of manual manipulation required to inflate and deflate the balloon, physician-to-physician variability is unavoidable. Thus, over the course of multiple inflations and deflations of the balloon, there will be a great variability in the rise and fall of blood flow in the blood vessel. Normalizing the blood flow, i.e. the rate of inflation, pressure of inflation, and rate of deflation across physicians can be critical to the efficacy of post-conditioning. In addition to the cumbersome nature of actuating inflation and deflation of the angioplasty catheter, the speed of inflation is limited by the physical capability or limitations of the treating physician to rapidly rotate the screw piston. Given that many sequential inflations and deflations are needed during a post-conditioning, use of an angioplasty catheter has many drawbacks. As a result much time is lost in the process of using a conventional angioplasty catheter for post-conditioning.

Use of a conventional angioplasty catheter can also result in significant operator-to-operator variability in inflation time, pressure of balloon, size of balloon, and deflation time. A system which normalizes the inflation time, pressure, size and deflation time is required, while still allowing operator control of the duration of inflation. Lastly, angioplasty balloons, especially rapid exchange balloons, do not have any means to deliver drug distal to the balloon without the added steps of removing the guidewire and later replacing the guidewire.

Additionally, coronary retroperfusion also may be used as to preserve ischemic myocardium. Retrograde blood flow through the coronary venous system may be augmented by coronary ostial occlusion.

A need exists for a catheter system that is capable of reperfusion and retroperfusion to restore blood flow after an ischemic event in an intermittent and gradual fashion with ease and efficiency, while allowing the option of drug delivery distal to the balloon over a standard length guidewire.

SUMMARY OF INVENTION

In accordance with one embodiment of the disclosure, a system is provided that can be used for reducing or preventing reperfusion injury to a patient. The system includes a catheter including an elongate shaft having a proximal end, a distal end and a length therebetween. The elongate shaft includes an inflation lumen and an independent deflation lumen in fluid communication with an expandable member. In some embodiments, the catheter further includes a guidewire lumen and a drug delivery or infusion lumen.

An expandable member is disposed on the elongate shaft, for example, at or near the distal end of the shaft. The system provides the physician the capability to sequentially inflate and deflate the expandable member, e.g., balloon, without the need to change the apparatus and/or the balloon. The system also eliminates physician-to-physician variability by providing repeatable, reproducible inflation and deflation of the expandable member. In this manner, unlike an angioplasty catheter, the physician treating a patient for ischemia is capable of easily and reproducibly inflating and deflating the expandable member to prevent or at least reduce reperfusion injury. In this regard, the physician can inflate and deflate the expandable member pursuant to the methods of preventing reperfusion injury disclosed herein and in U.S. Publication No. 2004/0255956 to Vinten-Johansen, for example, the disclosure which is incorporated herein.

In one embodiment, the expandable member is a balloon. The balloon has a length less than about 10 mm, preferably less than about 6 mm, and more preferably less than about 4 mm. In one embodiment, the balloon can be a one-size-fits-all balloon such that the physician need not size the balloon to the blood vessel to be treated. In this regard, however, the balloon must be formed from a compliant polymeric material. The balloon, in some embodiments, molds to the shape of the blood vessel in which it is disposed and inflated. In some embodiments, the balloon is configured to occlude a blood vessel when the balloon is inflated with less than about 1 atmosphere of pressure. The blood vessel can be centric or eccentric. During successive inflation and deflation of the balloon, blood flow is pulsated or modulated through the blood vessel to the organ or tissue of the patient suffering from an ischemic event. During the pulsating or modulating of blood flow from rapid inflation and deflation of the balloon, normal perfusion of the organs and tissues that did not suffer an ischemic event is maintained.

In some embodiments, the balloon is configured to occlude a blood vessel having a diameter of about 2 to 10 mm, depending on the application. The occluded blood vessel can be part of the coronary, peripheral, or cerebral vasculature. For example, the balloon can have various configurations including spherical, triangular, conical, elliptical in shape before or during inflation. In some embodiments, the balloon has a substantially spherical shape while inflated, despite having other configurations pre-inflation. In this manner, the one-size-fits-all compliant balloon can take a spherical shape when inflated in a larger blood vessel, and conform to a smaller blood vessel by taking a more elongated shape in the narrower blood vessel.

The balloon is capable of substantially maintaining its configuration after sequential, multiple inflation and deflation cycles. In this manner, the balloon wall maintains sufficient elasticity for multiple inflation and deflation cycles. In some embodiments, the system is configured to fully inflate the balloon in about 5 seconds or less. In some embodiments, the balloon is fully inflated in about 1 second. This rapid inflation and deflation capability renders the catheter optimal for procedures such as post-conditioning.

In some embodiments, the deflation of the balloon is assisted by Venturi action. In one such embodiment, the catheter can be configured to induce Venturi-assisted flow of fluid from the deflation lumen to deflate the balloon. The system can be configured to create a vacuum to assist deflation of the balloon. In this regard, rapid deflation from the balloon can be effectuated. The system can be configured to deflate the balloon in about five seconds or less. In some embodiments, the system can deflate the balloon in less than about 2 to 3 seconds. In one embodiment, the catheter can include a pulse valve disposed between the inflation and independent deflation lumen to effectuate a Venturi effect for rapid deflation.

As described, the catheter includes at least an inflation lumen and a deflation lumen along a length thereof. In some embodiments, the deflation lumen has a diameter larger than a diameter of the inflation lumen. For example, the diameter of the deflation lumen can be about twice or double the diameter of the inflation lumen. In some embodiments, the catheter further includes a guidewire lumen. In this manner, the catheter can include a rapid exchange configuration such that the guidewire lumen is disposed along the distal shaft segment of the catheter shaft to about an intermediate section of the catheter shaft. In other embodiments, the guidewire lumen can be disposed along substantially the entire length of the catheter shaft to provide an over-the-wire catheter configuration. The guidewire lumen has a diameter sufficient to house a standard 0.14 guidewire, or any other guidewire. In some embodiments, the guidewire lumen has a diameter larger than the deflation lumen. In some embodiments, the guidewire lumen, inflation lumen, and deflation lumen, each have a different sized diameter. The catheter can further include a drug delivery lumen. The drug delivery lumen can have a diameter size that is different than the other lumens.

In another embodiment, the system includes an indicator, such as a balloon pressure marker in communication with the deflation lumen. The indicator indicates to a physician when the expandable member, such as a balloon is inflated or deflated, even when the catheter balloon is in vivo.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 3A-3E are schematic illustrations of the catheter shaft in accordance with embodiments of the disclosed subject matter;

DETAILED DESCRIPTION OF EXEMPLARY EMBODIMENTS

Figure 1:
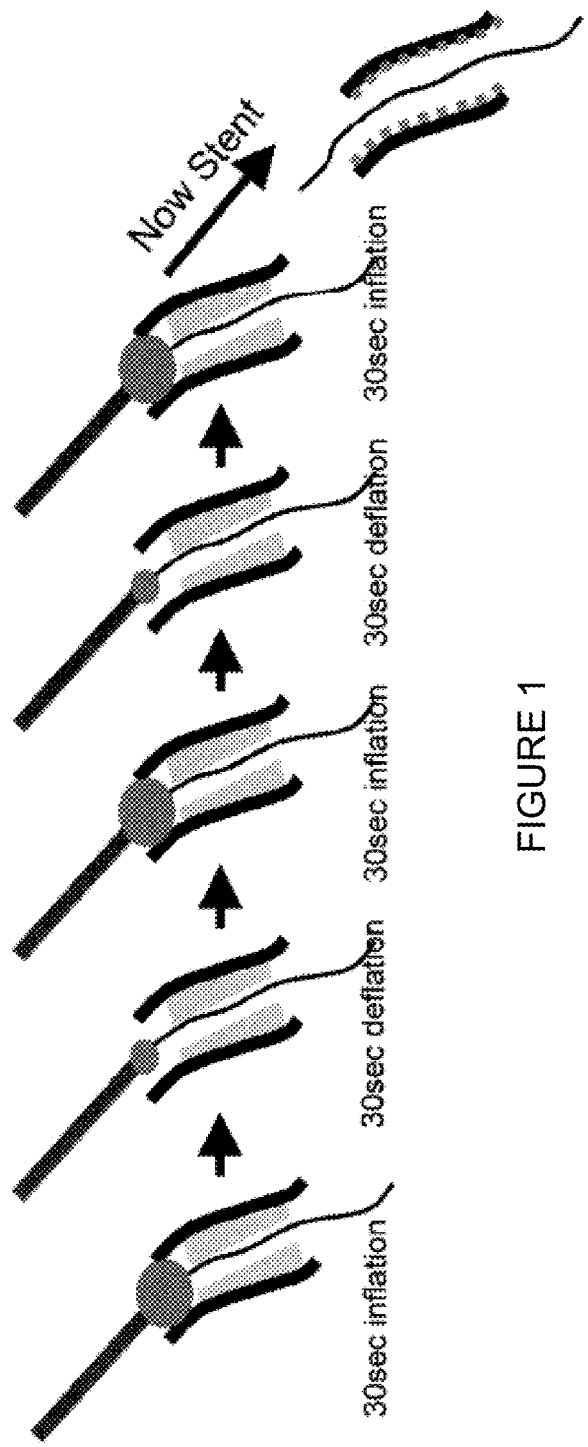
FIGS. 1 and 1A are schematic illustrations of a post conditioning method in accordance with one embodiment of the disclosed subject matter.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter.

I. System Overview

In accordance with the invention, a system is configured to permit sequential, such as intermittent and repeated, inflation and deflation of an expandable member, such as a balloon. In some embodiments, the sequential inflation and deflation of the balloon is achieved by single-touch actuation. The term "single-touch" as used herein means that actuation of inflation and deflation of the expandable member can be achieved by a single switch, single button, or other single point of actuation. In this regard, the user simply presses or otherwise actuates an actuator to inflate the balloon, and presses it again to actuate deflation of the balloon. Thus, unlike the angioplasty catheter that generally requires sizing, prepping, and inflating by rotation of a screw on the indeflator, one embodiment of the present system avails itself of quick use without the need for preparation.

A step by step comparison shows that while an angioplasty balloon catheter requires many steps to size, prep, remove air bubbles and use the device, a catheter system in accordance with an embodiment of the present system is much more efficient.

In this regard, one embodiment of the system provides physicians with an efficient, easy to use catheter designed for rapid, sequential or repeated inflation and deflation of a balloon, such as for reducing or preventing reperfusion injury to an organ or tissue after an ischemic event in the context of preventing or reducing reperfusion injury, or for other applications. For applications in which the system is employed for post-conditioning applications, the system can be employed to (1) stop perfusion to the organ or tissue for an amount of time, and (2) permit perfusion to the organ or tissue for another period of time, repeating the stopping and perfusion steps sequentially, and (3) deliver beneficial agents or contrast to areas distal to the balloon.

Beneficial agents include drugs, proteins, therapeutic agents, and other agents that promote health or recovery. Some non-limiting examples include calpain inhibitors, endothelin receptor blockers, pH stabilizing agents, antithrombotic agents, and proteins, cells or vectors including angiogenic factors. Certain non-limiting calpain inhibitors and other beneficial agents are disclosed in WO 98/25899, WO 98/25883, WO 9954305, WO 99/54310, WO 99/61423, WO 00/78933, WO 2008/080969, WO 2009/083581, U.S. Publication Nos. 2006/0205671 and 2008/0097385, each of the disclosures of which are incorporated herein by reference. Other examples of beneficial agents include nitroglycerin, epinepharin, lydocaine, heparin, hirudin, and ReoPro™. As will be recognized in the art, however, other drugs or beneficial agents may be employed.

In one embodiment, the catheter system as described herein is useful for post-conditioning methods. In this manner, the expandable member, preferably a balloon, is configured to occlude a blood vessel during expansion or inflation of the expandable member, and then permit resumption of perfusion of the blood flow during contraction or deflation of an expandable member. The occluded vasculature can include a venous blood vessel as in retroperfusion, or an arterial blood vessel such as in reperfusion. The occluded blood vessels may be from the coronary, peripheral, or cerebral vasculature. As illustrated in the schematic of FIG. 1, in one embodiment post conditioning is achieved by inflating and deflating the catheter balloon proximal to a lesion for one or more cycles of

| Steps | Typical Angioplasty System | One Embodiment of the System |
|---|---|---|
| 1. | Size vessel proximal to lesion | Get package containing system |
| 2. | Determine size of balloon needed | Open Box containing system |
| 3. | Get Box(s) | Unwrap Product |
| 4. | Look Up Compliance Chart | Engage Pressure |
| 5. | Choose final size | Advance to target lesion over guidewire |
| 6. | Open box containing angioplasty system | Flip switch On (no purge required, no air bubbles if carbon dioxide fluid used) |
| 7. | Unwrap product | Flip switch off |
| 8. | Purge Indeflator | Repeat steps 6 and 7 to sequentially inflate and deflate |
| 9. | Connect Balloon to Indeflator | |
| 10. | Prep Balloon (1st time = 3 steps) | |
| 11. | Prep Balloon (2nd time = 3 steps) | |
| 12. | Confirm no air bubbles | |
| 13. | Advance to target lesion | |
| 14. | Lock Indeflator | |
| 15. | Twist handle while watching dial until target pressure diameter curve is reached (about 8 atm) | |
| 16. | After 30 seconds, unlock Indeflator | |
| 17. | Pull vacuum | |
| 18. | Repeat steps 14-17, repeat prep balloon if bubbles seen | | about 10 to 60 seconds. These cycles are repeated as necessary to perform the post-conditioning therapy. For example, an expandable member is sequentially contracted and expanded such as to permit perfusion for about 10 to about 60 seconds and stop perfusion for about 10 to about 60 seconds for a one or more cycles. In some embodiments, the cycles are repeated for about 3 to about 10 cycles. As shown in FIG. 1, in one embodiment, the cycles for both inflation and deflation are for a period of about 30 seconds each. Other post-conditioning methods can be employed, however, such as post-conditioning methods described in U.S. Patent Publication No. 2004/0255956 and 2007/0160645 to Vinten-Johansen et al., the disclosures of which is incorporated herein by reference for all purposes. In some embodiments, the catheter is designed to post condition a stented blood vessel without changing the dimension of the implanted stent. In this manner, the expandable member is a compliant balloon as described below, which does not negatively affect the implanted stent during post-conditioning cycles of inflation and deflation of the balloon.

Figure 1A:
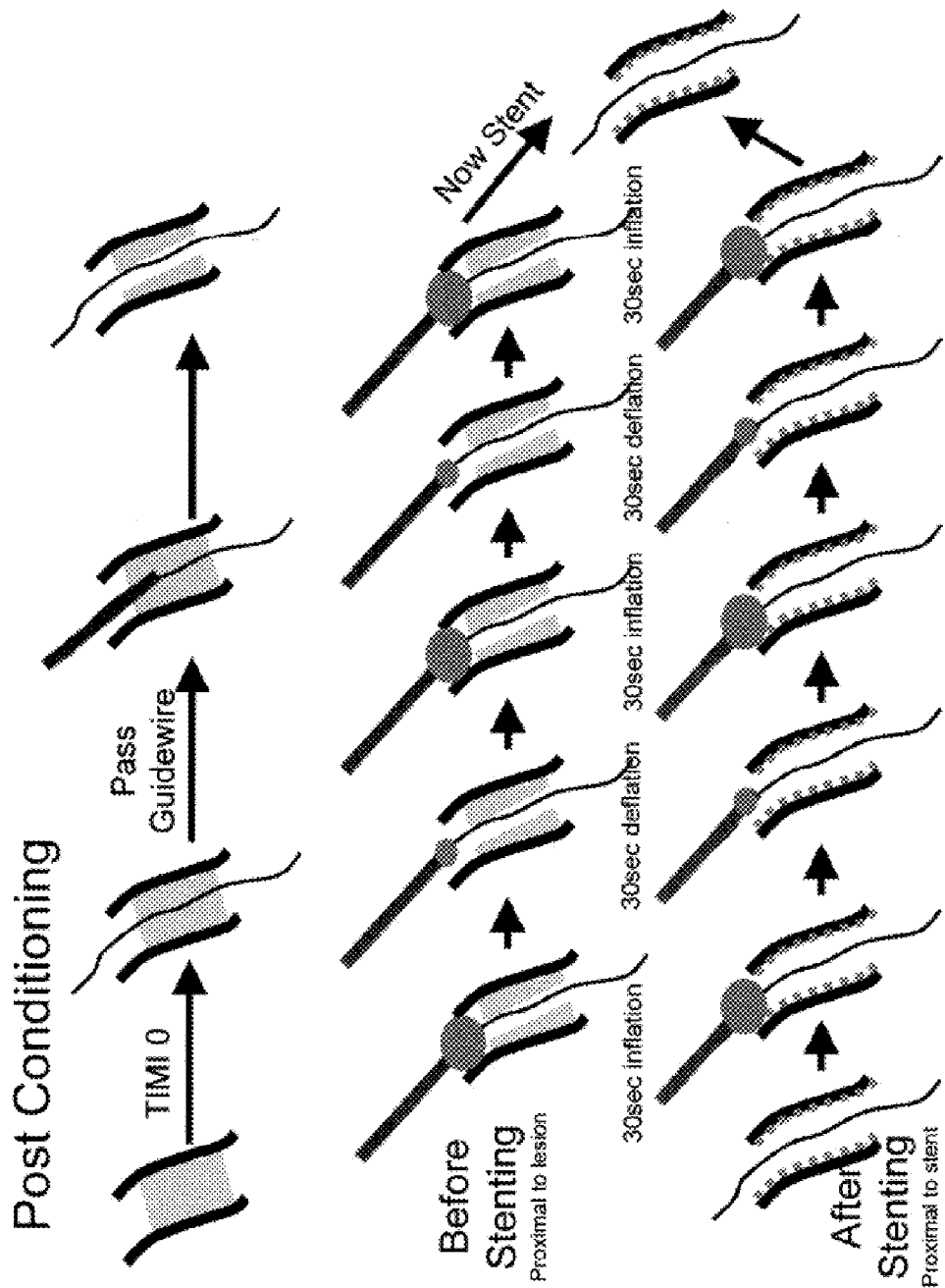

As illustrated in FIG. 1A, the post conditioning technique can be employed prior to stenting a blood vessel or subsequent to stenting a blood vessel.

With regards to post-conditioning prior or after stenting, the post conditioning device embodied herein will not dislodge the plaque. With regards to post-conditioning after stenting, the post conditioning can occur proximal to the stent, distal to the stent, and/or inside the stent. Advantageously, the catheter device embodied herein does not alter the shape or dimension of the deployed stent when post conditioning is employed within the stented vessel.

Accordingly, embodiments of the catheter of the invention can be used for post-conditioning before or after placement of a stent in a blood vessel.

Figure 2A:
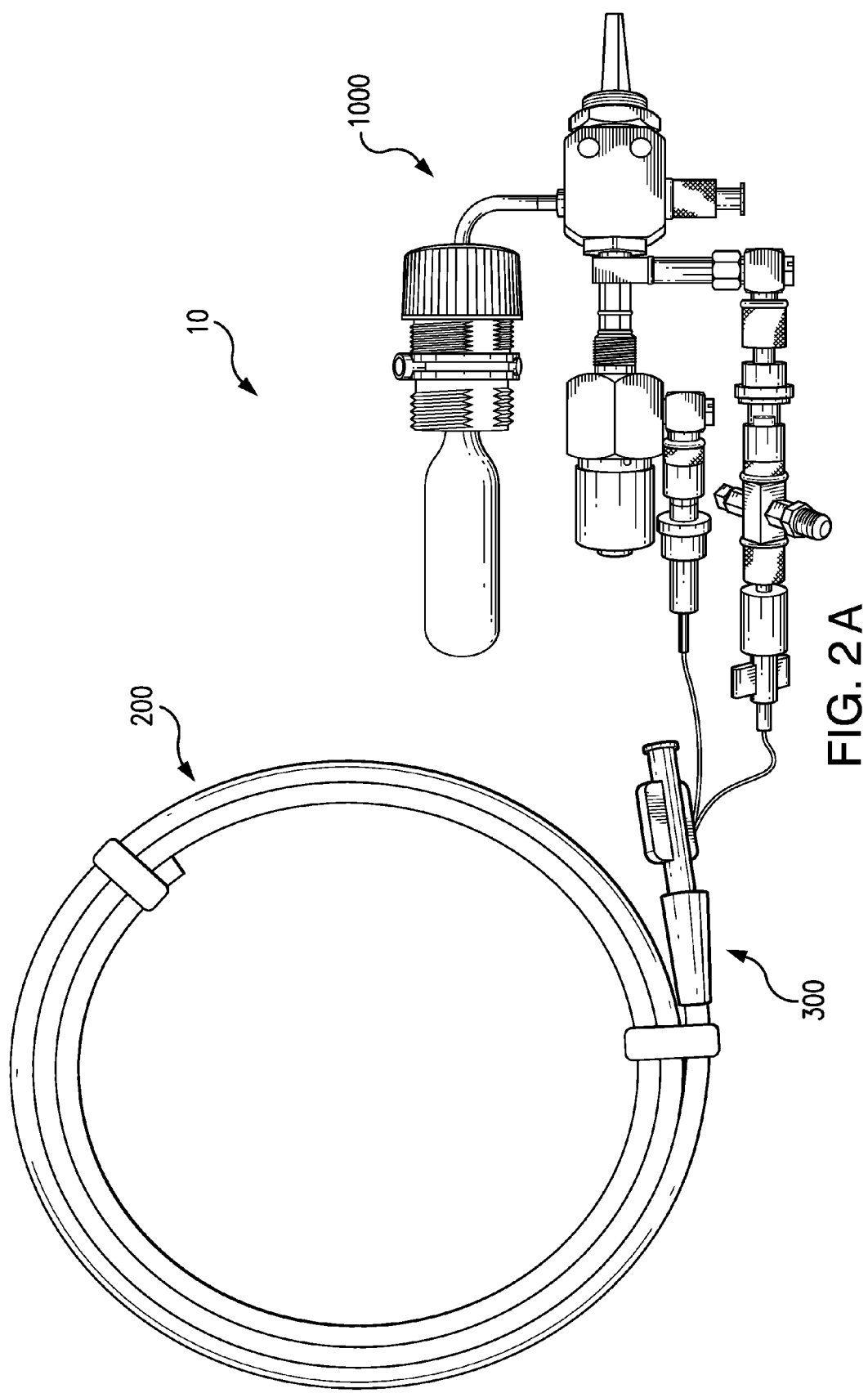
FIGS. 2A-2B are schematic views of the system in accordance with one embodiment of the disclosed subject matter.
Figure 2B:
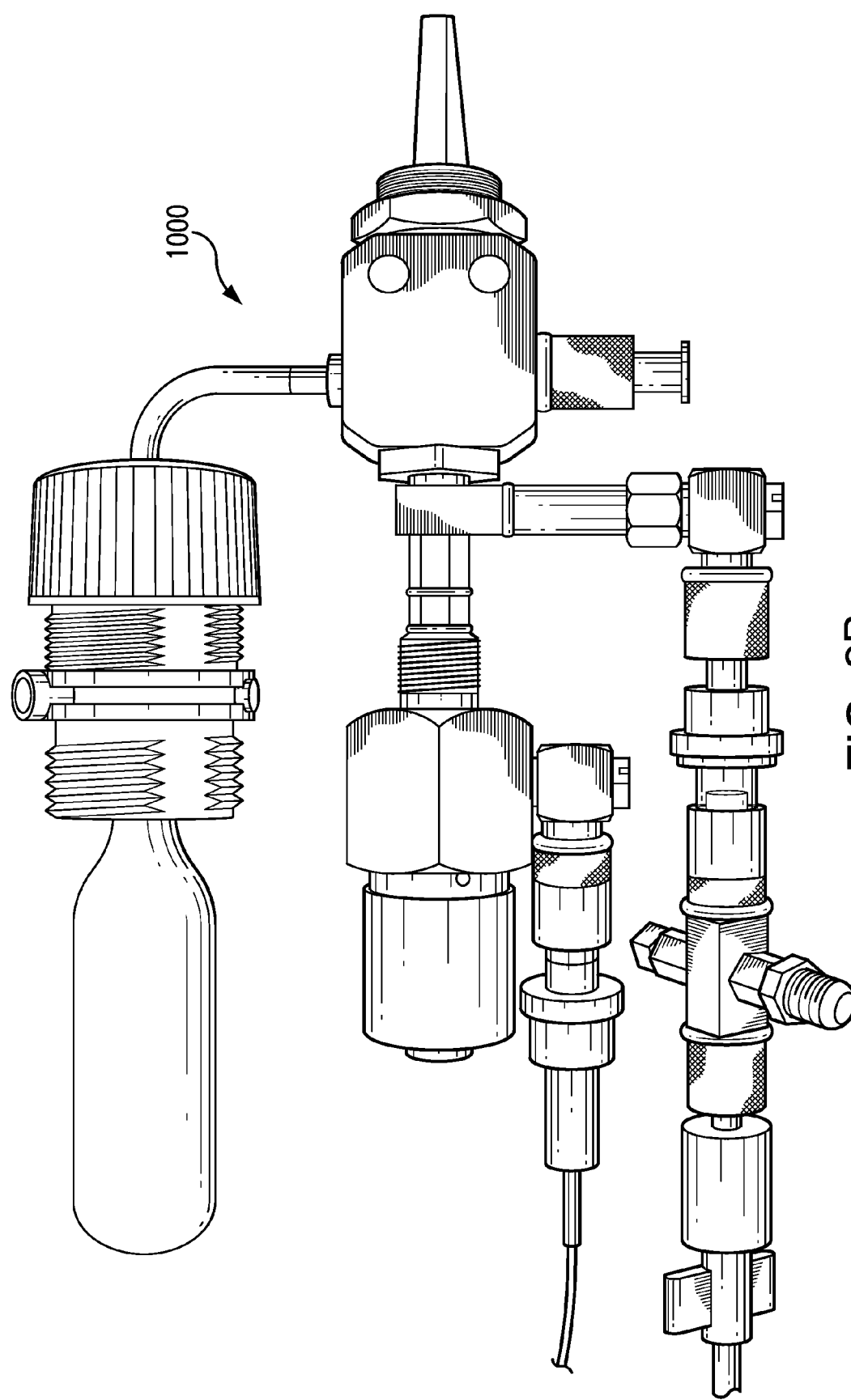

As shown in FIG. 2A, the catheter system 10 generally includes a catheter having an elongate shaft 200, an expandable member 300 and a fluid circuit including a control system 1000 (FIG. 2B) housed in a handle (not shown). In some embodiments, handle 100 (FIG. 5A) is non-removably attached to the catheter system such that a single unitary device is provided. Advantageously, the unitary device is packaged in a ready-to-use state. In some embodiments, expandable member 300 is disposed at a distal section of the elongate shaft of the catheter.

The elongate shaft 200 includes at least two lumen, as better seen in FIGS. 3A to 3C. In one embodiment, the at least two lumen include an inflation lumen and a separate dedicated independent deflation lumen. Both the inflation lumen and the independent deflation lumen are in fluid communication with the interior portion of a balloon 300. In this regard, an inflation fluid of any pressurized fluid, such as carbon dioxide, noble gases including helium, neon, and pressurized liquids such as saline or contrast agents, is introduced into the balloon 300 via the inflation lumen to inflate the balloon and then exits the balloon via the independent deflation lumen. The independent deflation lumen allows for rapid deflation of the balloon and in one embodiment is configured for Venturi-assisted deflation, as described below.

Figure 5A:
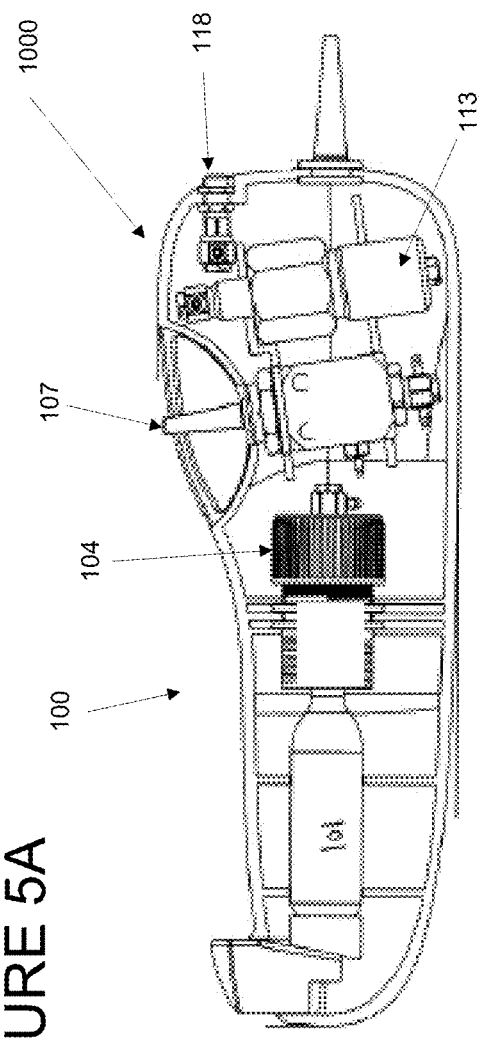
FIGS. 5A and 5B are cross sectional views of some embodiments of the handle in accordance of with the disclosed subject matter.
Figure 5B:
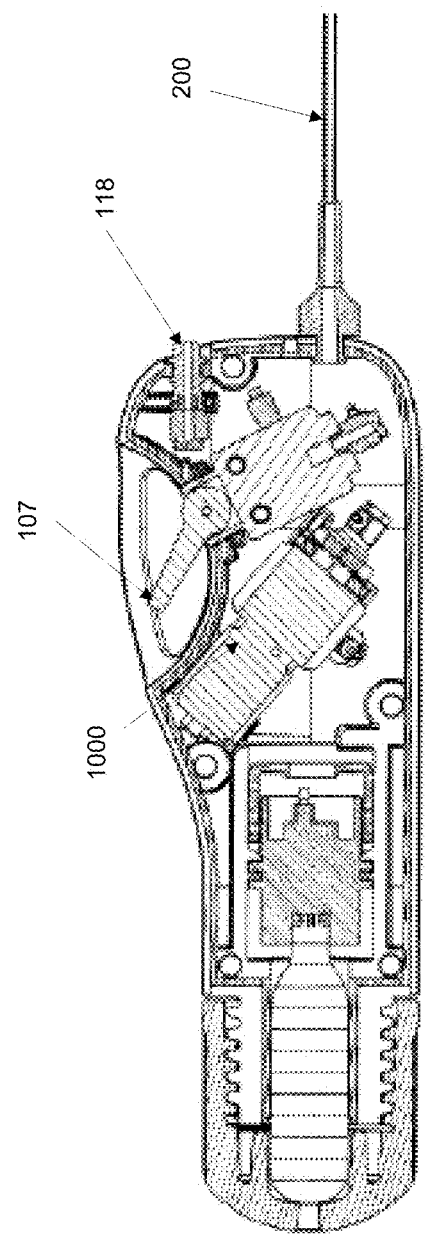

A handle 100 is disposed at or near the proximal end of the catheter and houses the control system 1000 of the fluid circuit (FIGS. 5A and 5B). Handle 100 is configured to provide a physician with the ease of automatic, sequential inflation and deflation of expandable member 300 by, in some embodiments, a one-touch actuator. In this manner, the one-touch actuator can be a switch, button, lever, or other device adapted to permit a user to inflate expandable member 300 when actuated in a first position or direction, and to deflate expandable member 300 when actuated in a second position or direction. The one-touch ease of sequential inflation and deflation of expandable member 300 can be achieved by adapting the catheter shaft to include an independent inflation lumen and separate independent deflation lumen. In some embodiments, the switch is configured such that the user cannot overinflate the expandable member 300. In this regard, the system can include a pulse valve that closes an outlet port to the expandable member when the expandable member is fully inflated thereby preventing over inflation. In this manner, when the balloon is fully inflated further actuation of the switch does not further inflate the balloon, thereby rendering the system "fool-proof" and effectuating reproducibility with relation to inflation of the expandable member.

In some embodiments, the handle 100 includes a control system 1000 of a fluid circuit disposed within the catheter device. The control system 1000 is configured to assist modulation of inflation fluid flow throughout the fluid circuit of the catheter system such as to effectuate inflation and deflation of the expandable member 300. In some embodiments, the fluid circuit and in particular the independent deflation lumen can be configured to induce a Venturi-assisted flow to rapidly deflate expandable member 300, as will be described below.

II. The Catheter Body

In accordance with one embodiment, as shown FIG. 3A, the catheter includes a generally elongate tubular shaft 200 having a proximal shaft segment 201 and a distal shaft segment 202 in fluid communication. Proximal shaft segment 201 and distal shaft segment 202 can be formed from material having the same or similar hardness or durometer to provide a uniform flexibility along the catheter body. Alternatively, the proximal shaft segment and distal shaft segment can be formed from materials having different flexibilities to provide a catheter having a varied flexibility along a length thereof. For example but not limitation, the proximal shaft segment may be formed from a hypotube and the distal shaft can be formed from a polymeric material to provide increased flexibility along the catheter tubular shaft. As such, the proximal shaft and distal shaft segments can be formed from the same tube or alternatively can be two separate tubes connected or welded together to form a unitary tube. The catheter may comprise one or more polymers or polymer blends having different stiffness.

As illustrated in FIG. 3B, elongate shaft 200, in one embodiment, includes an independent inflation lumen 203 configured to provide a passage or flow of inflation fluid to an expandable member 300 disposed at or near the distal end 202 of the catheter shaft. Elongate shaft 200 can also include an independent deflation lumen 204 to provide a second fluid flow passage for the inflation fluid to outflow from expandable member 300 during deflation. In this manner, the sequential inflation and deflation of expandable member 300, and consequential stopping and starting of blood flow during post-conditioning techniques can be efficient and rapid. For example, in one embodiment of the system, the expandable member 300 can be inflated in five seconds or less, preferably one second or less, most preferably in ⅕th of a second or less. Further, the expandable member can be deflated in five seconds or less, and preferably three seconds or less, most preferably ¼ of a second or less. This rapid inflation and deflation of the expandable member provides advantages for post-conditioning techniques not available through use of the conventional angioplasty catheter.

The elongate shaft 200 can be formed in a number of shapes, for example, in one embodiment, the shaft can have a tubular configuration as shown in FIG. 3B. However, as would be known in the art other shapes can be employed, such as elliptical.

The elongate shaft 200 can further include guidewire lumen 205, for example, in addition to the inflation and deflation lumen. In this regard, guidewire lumen 205 can be configured to extend from a tip 400 at the distal end of elongate shaft 200 to a more proximal location of the elongate shaft 200 to provide an over-the-wire catheter. Alternatively, elongate shaft 200 may be formed to have a notch (not shown) disposed at a location between the distal end 202 and proximal end 201 of elongate shaft 200 to provide a rapid exchange catheter.

In accordance with another embodiment, elongate shaft 200 can further include a drug delivery lumen 206, such as for example, a drug infusion lumen configured to locally deliver beneficial agents such as those described above or other agents. In one embodiment, the beneficial agents are locally delivered to an area of a ischemic event. In other embodiments, the catheter lacks a drug delivery lumen and instead, a drug coated balloon is disposed on the catheter shaft for local delivery of a beneficial agent.

In some embodiments, the elongate shaft 200 includes four separate and independent lumen (e.g., inflation lumen 203, deflation lumen 204, guidewire lumen 205, and drug delivery lumen 206). However, other configurations can be employed. In some embodiments, the diameters of the lumen have different sizes. For example, in some embodiments, the deflation lumen has a diameter of about twice the size of the inflation lumen diameter. In one embodiment, as depicted in FIG. 3C, the diameter of the inflation lumen 203$d$ is about 0.100 mm, the diameter of the deflation lumen 204$d$ is about 0.200 mm, the diameter of the guidewire lumen 205$d$ is about 0.400 mm, and the diameter of the infusion lumen 206$d$ is about 0.300 mm. Accordingly, each lumen can be configured to have a different sized diameter, if desired.

In some embodiments, as illustrated in FIG. 3B, elongate shaft 200 can be formed from a single extrusion with a plurality of lumen, e.g., the four lumen as described above. As further shown, the four lumen can be oriented within the extrusion so that the extruded polymeric web 208 remaining between the lumen forms an "I-beam" cross section. An I-beam configuration provides efficient form for resisting both bending and shear in the plane of the polymeric web 208. In this manner, the plurality of lumen 203, 204, 205, 206 are configured as independent lumen physically spaced from one another by polymeric web 208 disposed therebetween. An advantage of the I-beam shape is that the catheter shaft is more resistant to bending when the catheter is pulled in a particular direction.

Figure 3E:
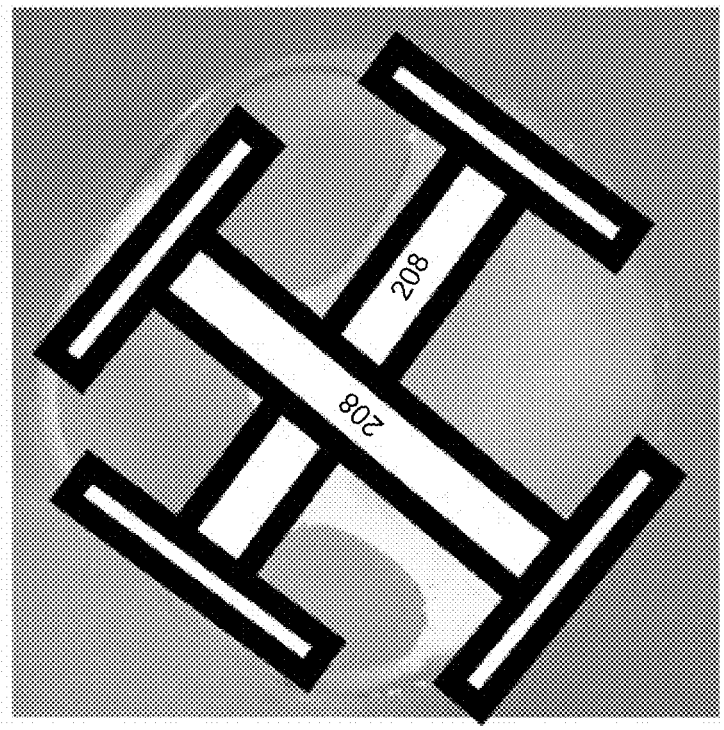
Figure 3D:
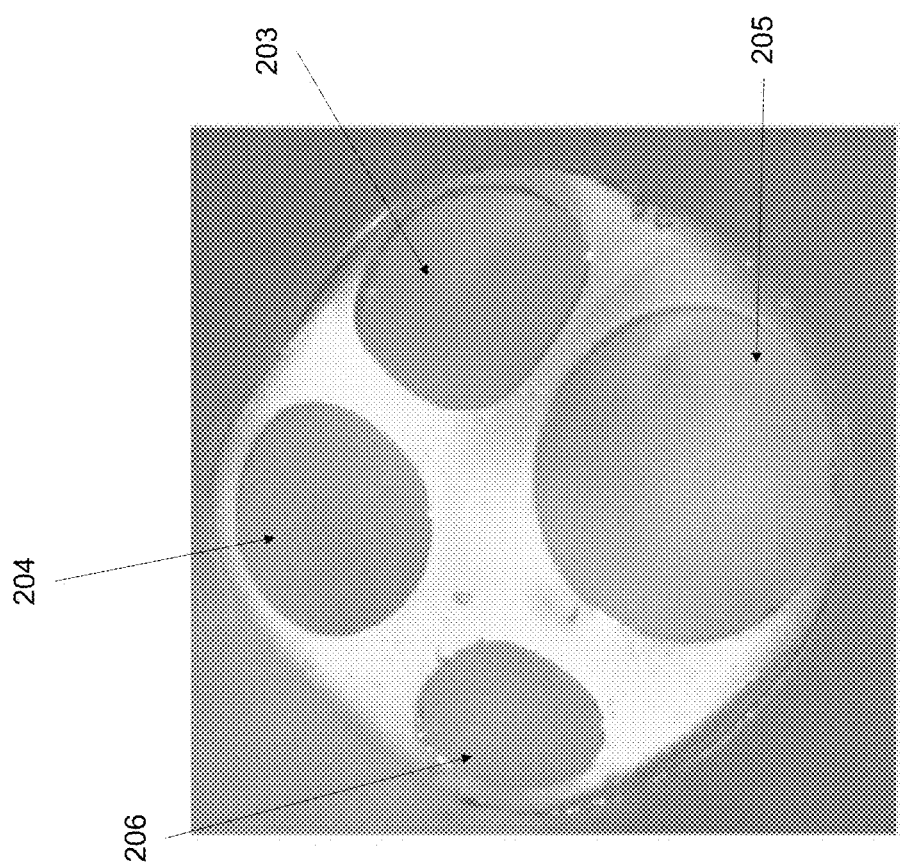

In some embodiments, the different sized lumen are arranged or oriented within the extrusion to form a pattern such that the largest sized lumen 205 is proximate each of the smaller sized lumen 203, 204, 206, as depicted in FIGS. 3B and 3C, such that the polymeric web 208 disposed between the lumen 203, 204 and 205 forms the I-beam pattern, as illustrated in FIGS. 3D and 3E. In some embodiments, the thickness of extruded polymeric web 208 is substantially equivalent to the bending moment of the shaft. A bending moment exists in a structural element when a moment is applied to the element so that the element bends. Moments and torques are generally measured as a force multiplied by a distance so they have as unit newton-meters (N·m), or foot-pounds force (ft-lbf). In this manner, it is believed that the elongate shaft 200 will resist bending equally, regardless of the direction of the bend to the catheter shaft. It is further believed that a catheter shaft without these features will bend to a different degree depending upon the orientation inside the vessel.

Elongate shaft 200 can further include a distal tip 400 (FIG. 3A) having a proximal end abutting or overlapping the distal end 202 of the catheter body. In one embodiment, catheter tip 400 includes one or more lumen. For example, in one embodiment, the tip 400 can include a first lumen aligned with guidewire lumen 205 of elongate shaft 200, and a second lumen aligned with infusion lumen 206. The guidewire lumen 205 is aligned with a lumen through the catheter tip 400 disposed at the distal end of the catheter shaft 202. These aligned lumens permit the catheter to ride over a guidewire. Furthermore, once properly inserted, the guidewire can be removed and fluid can be passed through the lumen.

In one embodiment, the tip 400 can be formed of a material softer than the material of the catheter such that the tip has sufficient column strength to resist buckling during insertion, but is sufficiently flexible to deform when the tip is subjected to axial or radial loads in the body in the absence of the guidewire. Catheter elongate shaft 200 is configured to enable the passage and the longitudinal translation of guidewire within lumen 205 during a surgical procedure.

Elongate shaft 200 can be produced from a variety of materials, including metal, plastic and composite materials. In one embodiment, proximal shaft 201 is manufactured as a metal tube, for example, as a stainless steel hypotube, and may be coated with a polymeric material such as PTFE. The metal tube may also be covered with a single or multilayered plastic material through one or more processes, including coextrusion, dipping, heat-shrinking, and electrostatic and thermal coating. In another embodiment, elongate shaft 200 is manufactured as a plastic tube. Materials suitable for use in the catheter tube include, but are not limited to, Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6,6, Nylon 6, Nylon 7,11, Nylon 11,12, and blends thereof); block copolymers; PEBA-types polymers, such as ELY, PEBAX, Ubesta, and blends thereof, and biodegradable polymers.

Suitable materials also include blends of the above mentioned materials as well as any composite materials, like dual-layers, tri-layers and multi-layers thereof. For example, catheter shaft may be produced from a tube comprising an outer layer made of Nylon and an inner layer made of a lubricious material such as polyethylene or PTFE. A metallic or nonmetallic braiding may also be included within or between layers of the catheter shaft.

Catheter tip 400 can be configured to provide atraumatic contact between elongate shaft 200 and a wall against which elongate shaft 200 may be pushed during a surgical procedure. The catheter tip can be configured as a soft tip, which in some embodiments, can be composed of a soft sleeve that is affixed on and that extends beyond distal end 202, or, alternatively, that is affixed on and extends beyond the lumen of elongate shaft 200. Typically, a soft tip is affixed through a welding process, but other affixing techniques are also included within the scope of the present invention, for example, adhesive bonding. Suitable materials for the sleeve can be chosen from any material suitable for producing elongate shaft 200. The sleeve may be manufactured from a material softer than elongate shaft 200, and may be formed from the same material as expandable member 300 or from a different material, for example, from any of the materials or combinations of materials described with reference to elongate shaft 200. In one embodiment, the sleeve is manufactured from a material having the same basic composition as, but a lower Shore durometer hardness than, the expandable member 300 material or the elongate tube 200 material. In another embodiment, the sleeve may be manufactured from a blend of PEBAX 55D and PEBAX 63D polymers. One skilled in the art will recognize that the sleeve may be manufactured from a variety of other materials according to the previous description of materials, for example, a polyurethane, a polyethylene, a polyolefin, a polyimide, a polyamide like Nylon, a block copolymer, or blends, or compositions or dual layers or multi-layers thereof.

III. The Expandable Member

In accordance with one embodiment of the invention, expandable member 300 is a polymeric balloon. Preferably, balloon 300 is a compliant balloon. Unlike a typical angioplasty balloon, which is configured to provide a new circular, open lumen, the polymeric balloon 300 of the embodiment should be sufficiently compliant to mold to the anatomy of the blood vessel. In this manner, balloon 300 can occlude a blood vessel having a diameter from about 2 mm to about 30 mm depending on whether the application is for the coronary, cerebral or peripheral blood vessels. In one embodiment, the balloon can occlude a blood vessel having a diameter from about 2 to about 4.5 mm for coronary or cerebral applications, with a pressure of about 0.5 to 2 atm. For peripheral applications, the balloon can occlude a blood vessel having a diameter from about 4 to about 30 mm, or any luminal orifice of the human body where occlusion of fluid flow could be therapeutic.

In one embodiment, the balloon is a one-size-fits-all balloon. In this regard, the balloon must be formed from a compliant polymeric material. For example and not limitation, the compliant balloon 300 can elongate when it is inflated within a narrow sized vessel, and can have a spherical shape when it inflated within a larger or wider blood vessel. Thus, the balloon is capable of molding to the blood vessel. Accordingly, the physician does not need to measure the artery of a patient prior to post-conditioning to size balloon 300 to the patient.

In one embodiment, balloon 300 is mounted to elongate shaft 200 of the catheter. Balloon 300 contains a hollow interior portion defining an inflation passage extending longitudinally therethrough to receive inflation fluid from inflation lumen 203 of elongate shaft 200. In one embodiment, the proximal portion of balloon 300 can be configured to taper radially inward at the proximal end and distal end of balloon 300. The proximal end and the distal end of balloon 300 are sized to mount and seal to respective portions of elongate shaft 200, while the balloon interior portion is configured for selective inflation from an unexpanded first condition to an expanded second condition as shown in FIG. 4B. Hence, the transverse cross-sectional dimension of balloon 300, in the expanded condition, is significantly greater than that of the inwardly tapered end portions of proximal end and the distal end of the balloon.

When balloon 300 is mounted to elongate shaft 200, inflation lumen 203 of elongate shaft 200 is in fluid communication with the inflation passage of balloon 300. Accordingly, by operating the one-touch control system at the proximal end of the catheter system, described below, the interior portion of the expandable member 300 can be selectively inflated from the first condition to the inflated second condition.

Distal shaft 202 of the elongate shaft 200 extends through the inflation passage of balloon 300, where a distal end of the catheter terminates distal to the distal end of the balloon 300. As best shown in FIG. 3A, distal shaft 202 extends longitudinally through the interior portion of the balloon 300, and defines the distal portion of the guidewire lumen 205 where it terminates at a distal port at a distal end of the elongate shaft 200. Hence, a guidewire (not shown) may extend through guidewire lumen 205 of the elongate shaft 200, and out through the distal port of the catheter distal end. This passage enables the catheter to be advanced along the guidewire that may be strategically disposed in a vessel.

Figure 4A:
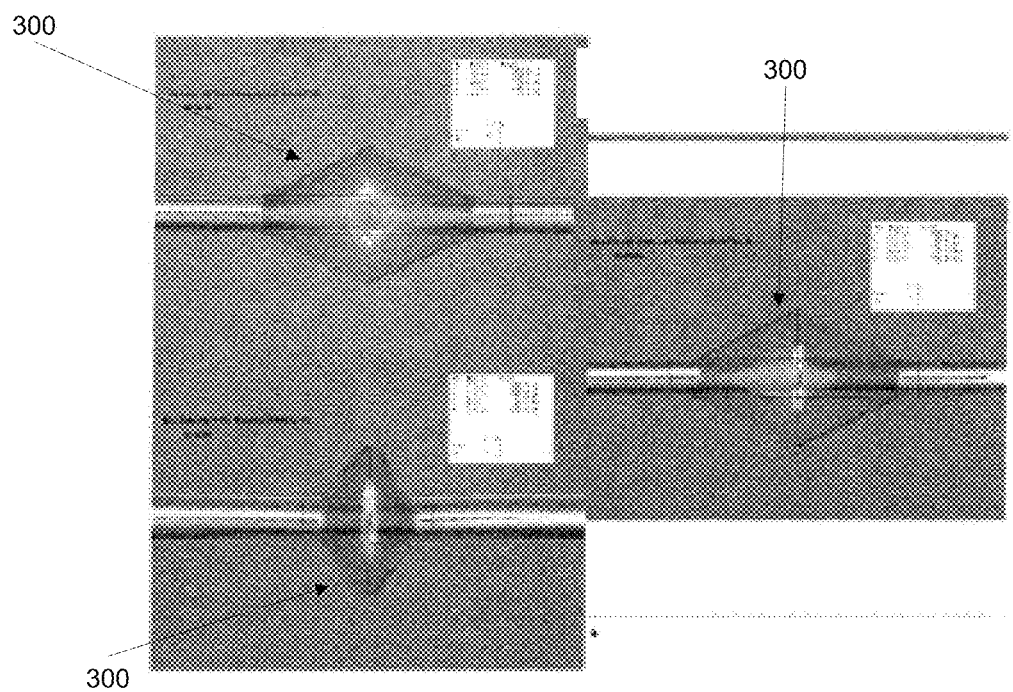
FIGS. 4A and 4B are perspective views of embodiments of balloons in accordance with the disclosed subject matter.
Figure 4B:
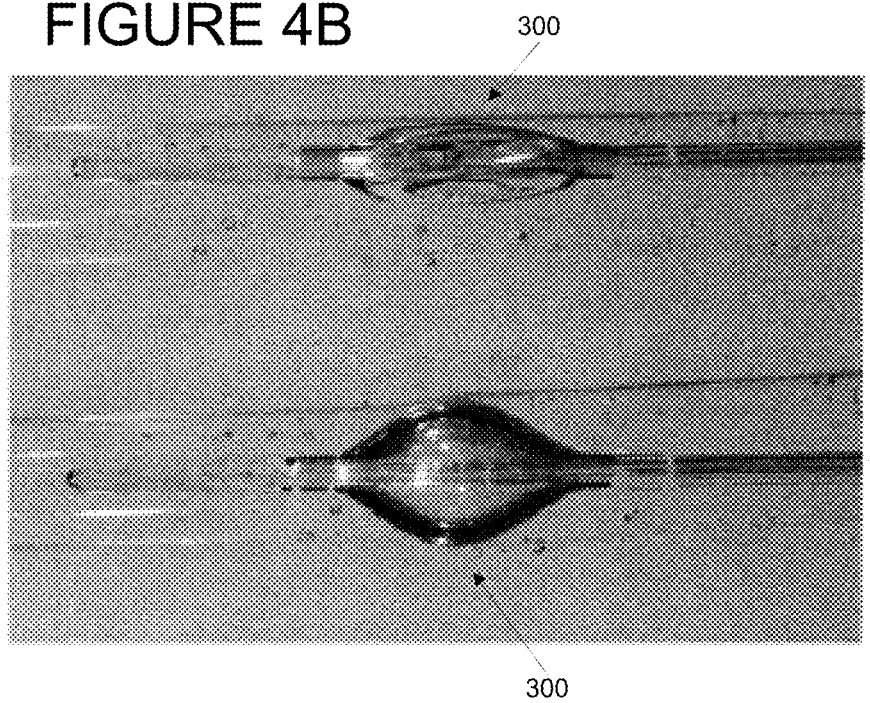

Balloon 300 can be formed in various shapes, as illustrated in FIGS. 4A and 4B. As shown, the shape of balloon 300 can be spherical, cylindrical, or polygonal. Various polymers may be selected for the formation of balloon 300, as would be known in the art. However, the balloon material should be sufficiently compliant such that balloon 300 can mold to the shape of the blood vessel.

In one embodiment, balloon 300 may be formed from a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D is presently preferred, and has a Shore durometer of 65D, an elongation at break of about 300%, and a high tensile strength at yield of about 10,000 psi. However, other suitable grades may be used, including TECOTHANE® 1075D, having a Shore hardness of about D75. Other suitable compliant polymeric materials include ENGAGE® (DuPont Dow Elastomers (an ethylene alpha-olefin polymer) and EXACT® (Exxon Chemical), both of which are thermoplastic polymers, elastomeric silicones, and latexes.

The compliant material may be crosslinked or uncrosslinked. The presently preferred polyurethane balloon materials are not crosslinked. By crosslinking the balloon compliant material, the final inflated balloon size can be controlled.

Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure.

In one embodiment, balloon 300 is formed from a low tensile set polymer such as a silicone-polyurethane copolymer. Preferably, the silicone-polyurethane is an ether urethane and more specifically an aliphatic ether urethane such as PURSIL AL 575A and PURSIL AL10 (Polymer Technology Group), and ELAST-EON 3-70A (Elastomedics), which are silicone polyether urethane copolymers, and more specifically, aliphatic ether urethane cosiloxanes.

In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. The diene polymer can be an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the invention include HT 501 available from Apex Medical, and neoprene (i.e., polychloroprene) available from Dupont Elastomers, including Neoprene G, W, T and A types available from Dupont Elastomers.

In one embodiment, the polymeric material is a compliant material such as, but not limited to, a polyamide/polyether block copolymer (commonly referred to as PEBA or polyether-block-amide). Preferably, the polyamide and polyether segments of the block copolymers may be linked through amide or ester linkages. The polyamide block may be selected from various aliphatic or aromatic polyamides known in the art. Preferably, the polyamide is aliphatic. Some non-limiting examples include nylon 12, nylon 11, nylon 9, nylon 6, nylon 6/12, nylon 6/11, nylon 6/9, and nylon 6/6. Preferably, the polyamide is nylon 12. The polyether block may be selected from various polyethers known in the art. Some non-limiting examples of polyether segments include poly(tetramethylene glycol), tetramethylene ether, polyethylene glycol, polypropylene glycol, poly(pentamethylene ether) and poly(hexamethylene ether). Commercially available PEBA material may also be utilized such as for example, PEBAX® materials supplied by Arkema (France). Various techniques for forming a balloon from polyamide/polyether block copolymer are known in the art. One such example is disclosed in U.S. Pat. No. 6,406,457 to Wang, the disclosure of which is incorporated by reference.

In another embodiment, the balloon material is formed from polyamides. Preferably, the polyamide has substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. Preferably, the polyamide is nylon 12. In yet another embodiment, balloon 300 is composed of several different layers, each one being a different polyamide or polyamide/polyether block copolymer.

In accordance with some embodiments, balloon 300 can be composed of a single polymeric layer, or alternatively, can be a multilayered balloon, such as those described in U.S. Pat. No. 5,478,320 to Ishida, U.S. Pat. No. 5,879,369 to Trotta, or U.S. Pat. No. 6,620,127 to Lee, the disclosures of which are incorporated herein by reference.

IV. The Handle and Fluid Circuit

Figure 5C:
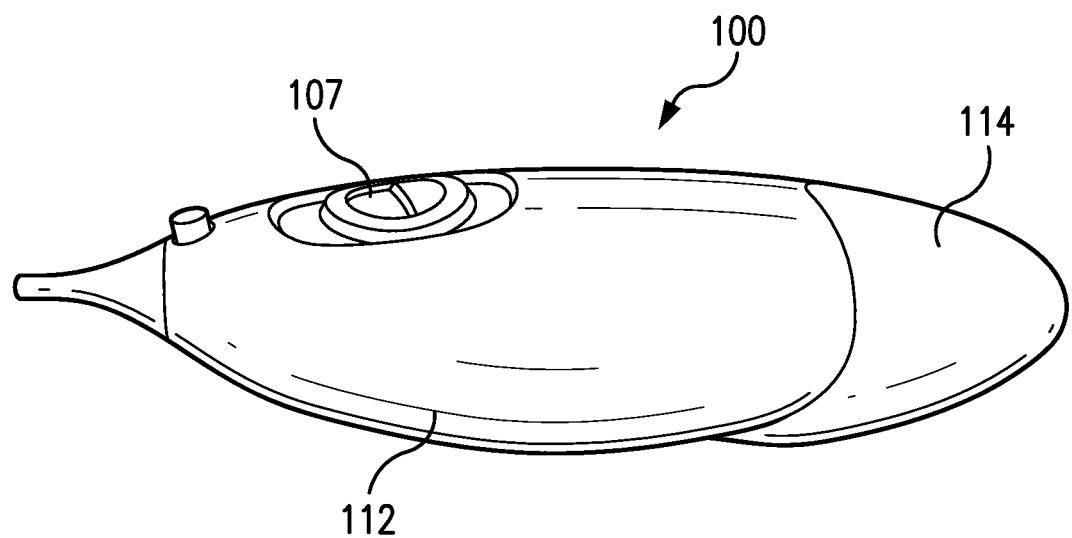
FIGS. 5C to 5R are perspective views of various embodiments of handles in accordance with the disclosed subject matter.
Figure 5D:
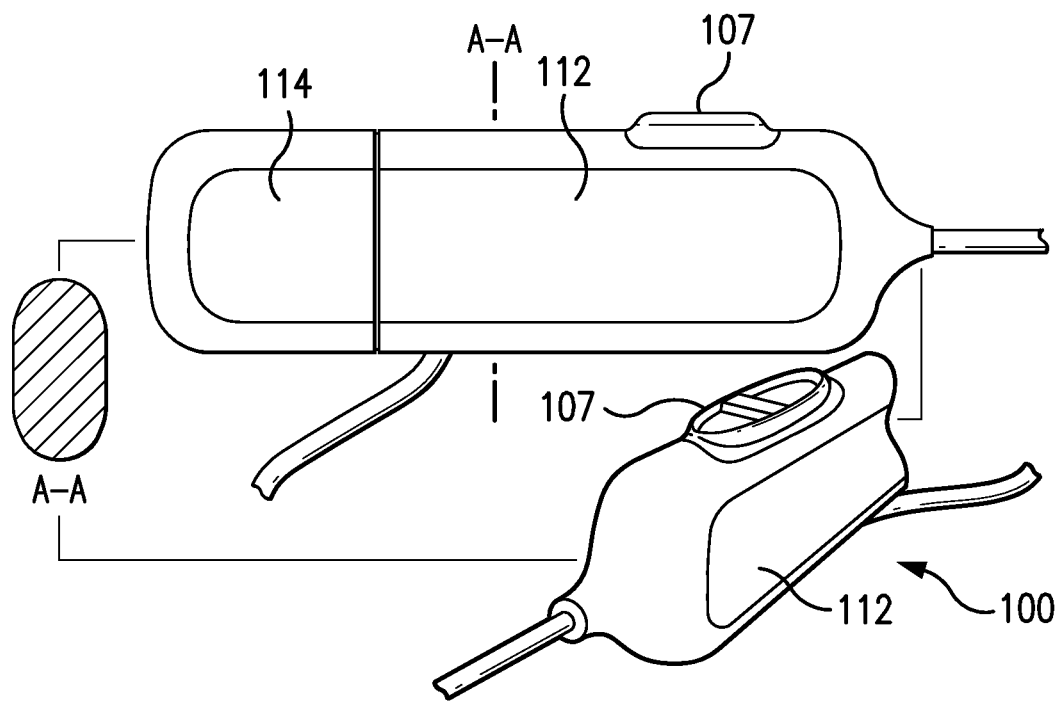
Figure 5E:
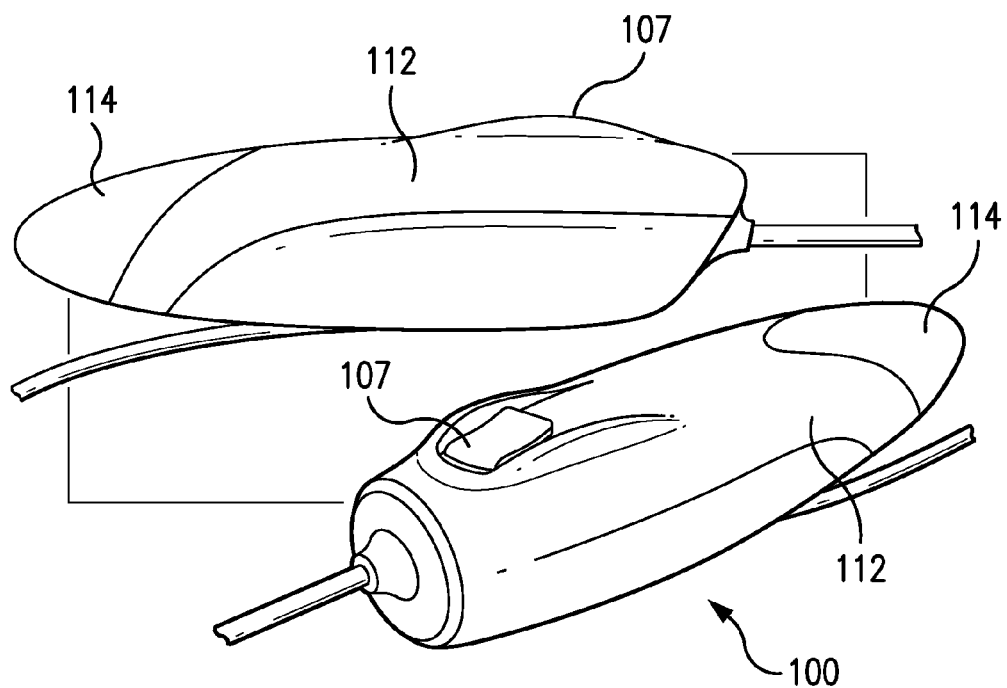
Figure 5F:
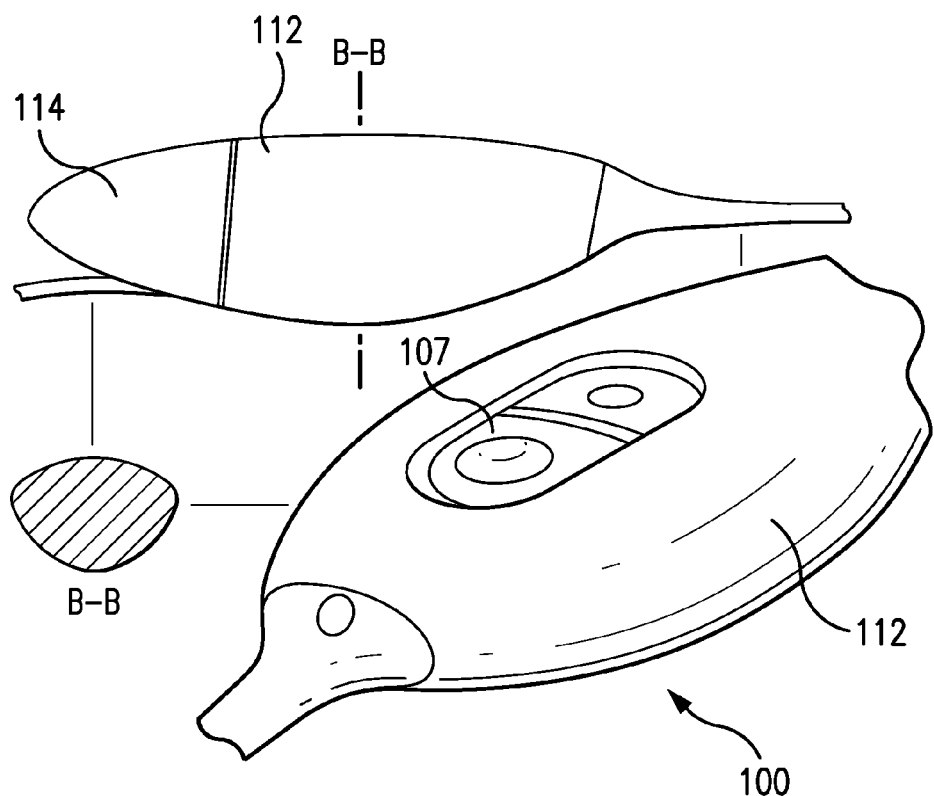
Figure 5G:
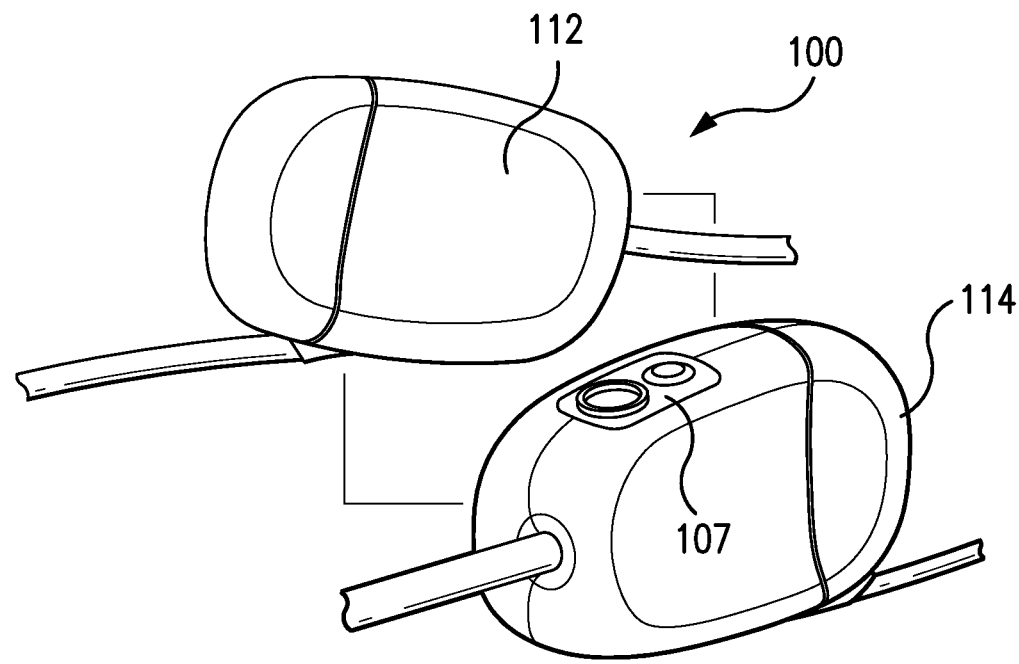
Figure 5H:
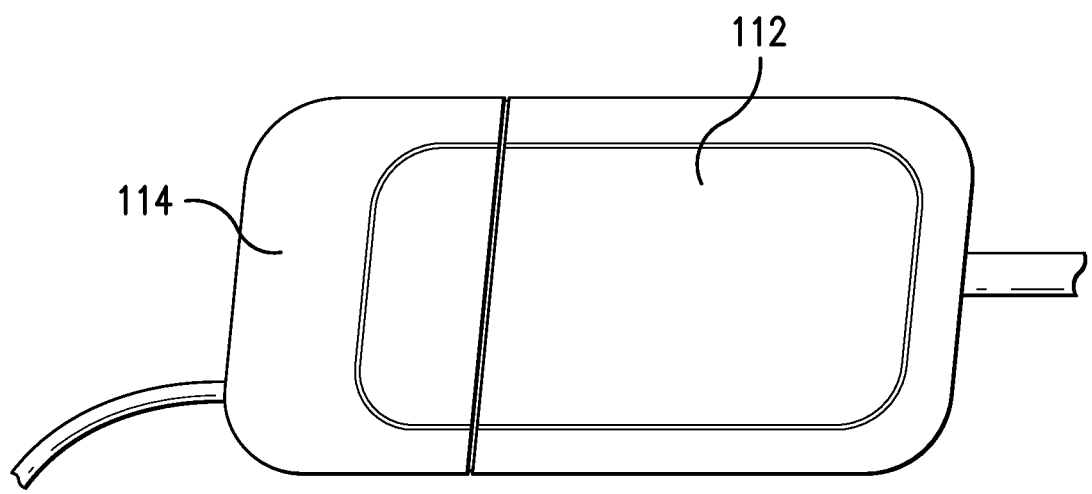
Figure 5I:
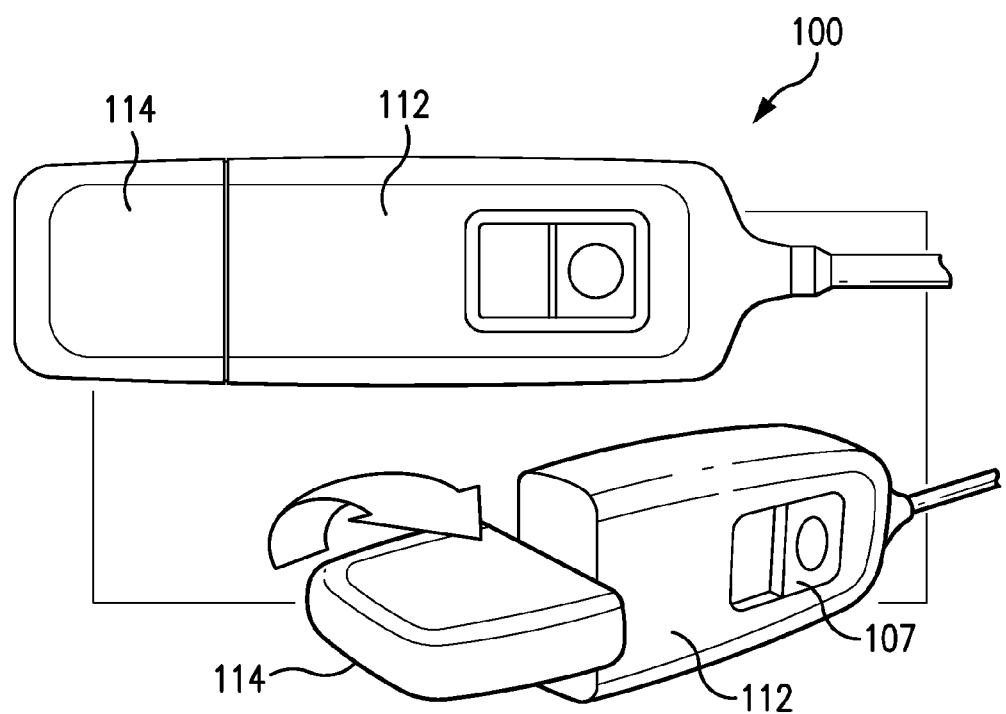
Figure 5J:
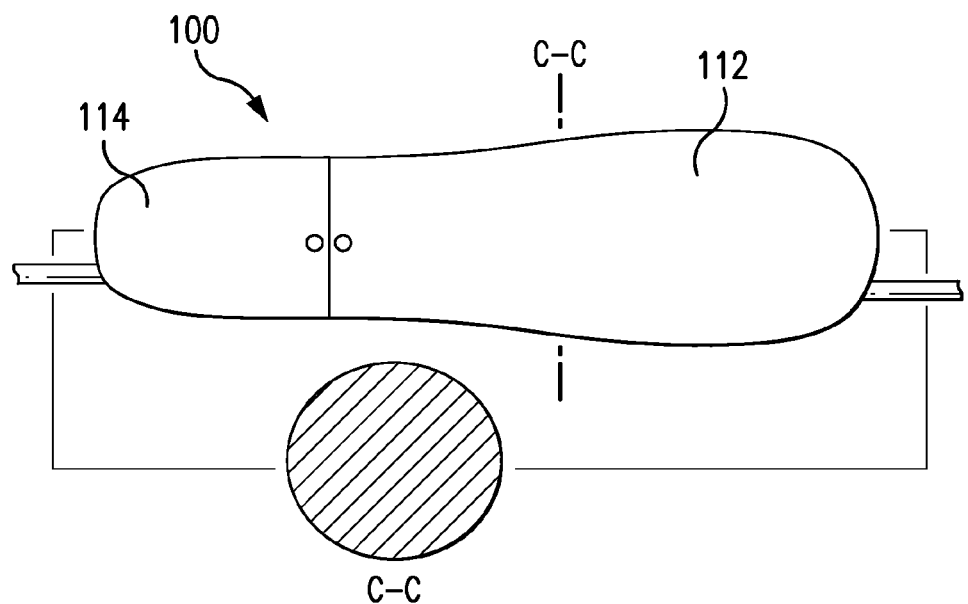
Figure 5K:
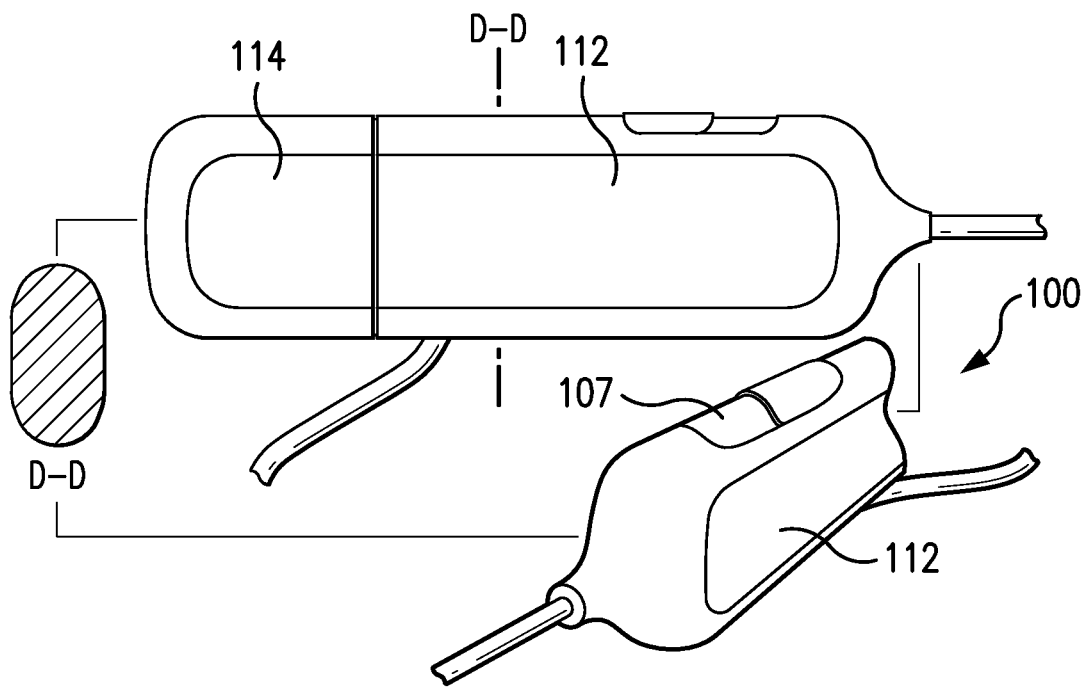
Figure 5L:
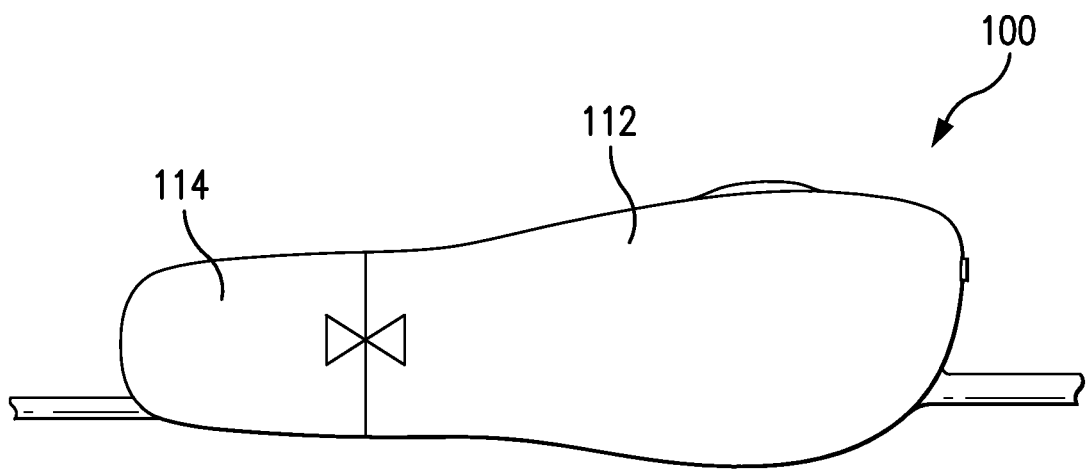
Figure 5M:
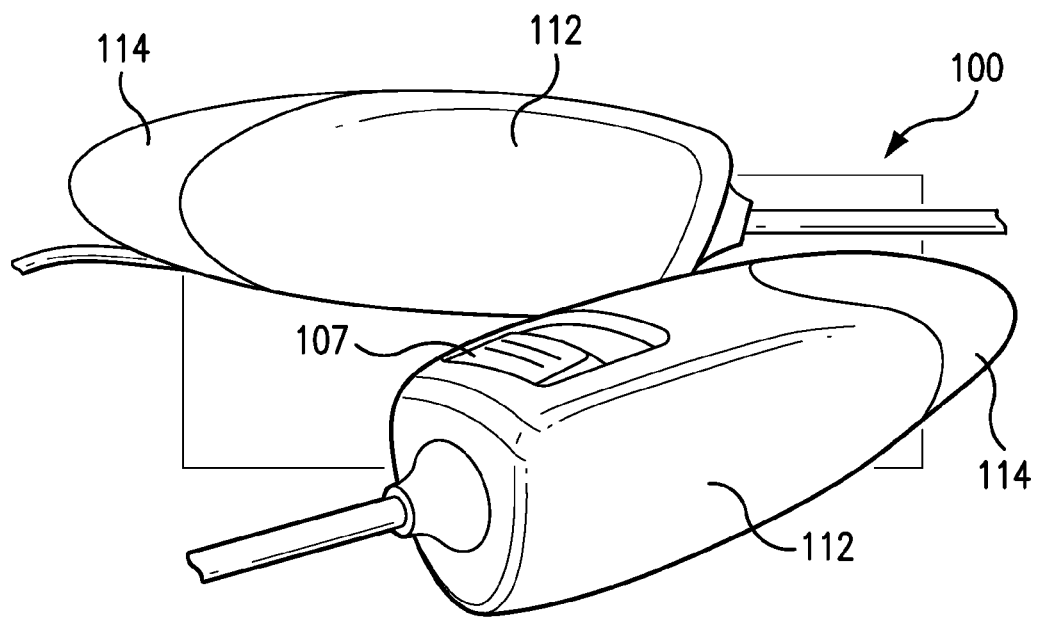
Figure 5N:
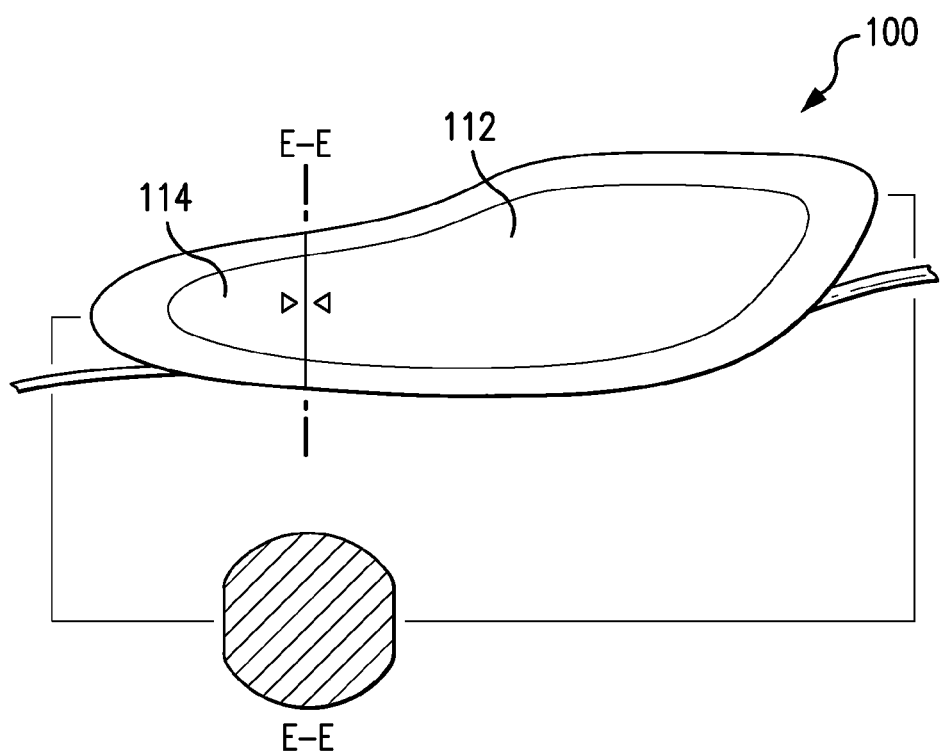
Figure 5O:
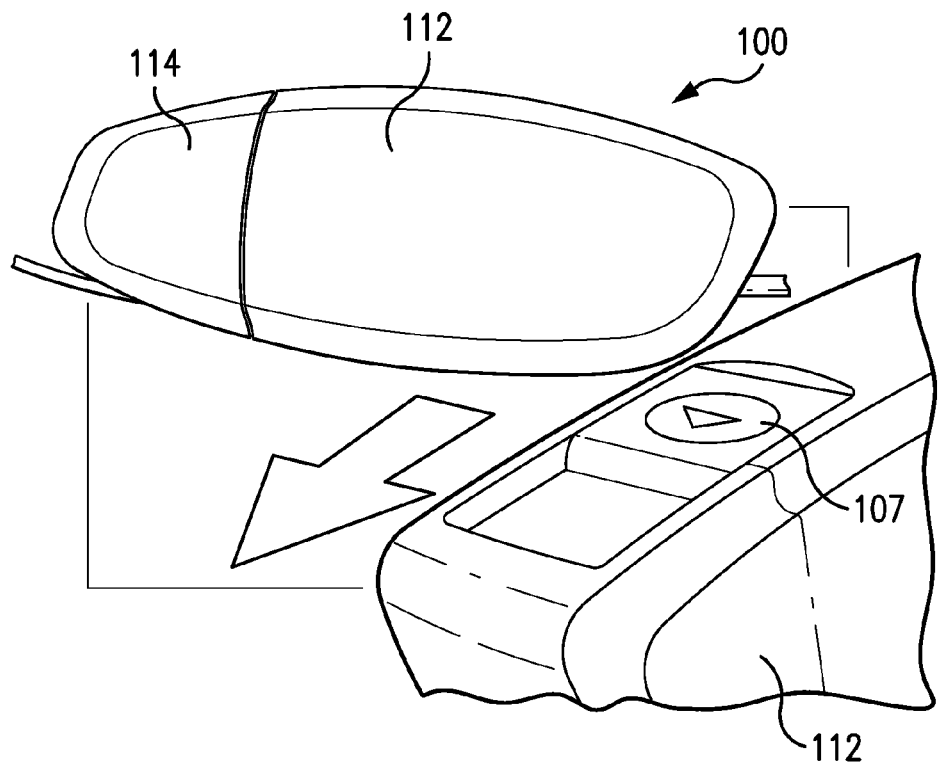
Figure 5P:
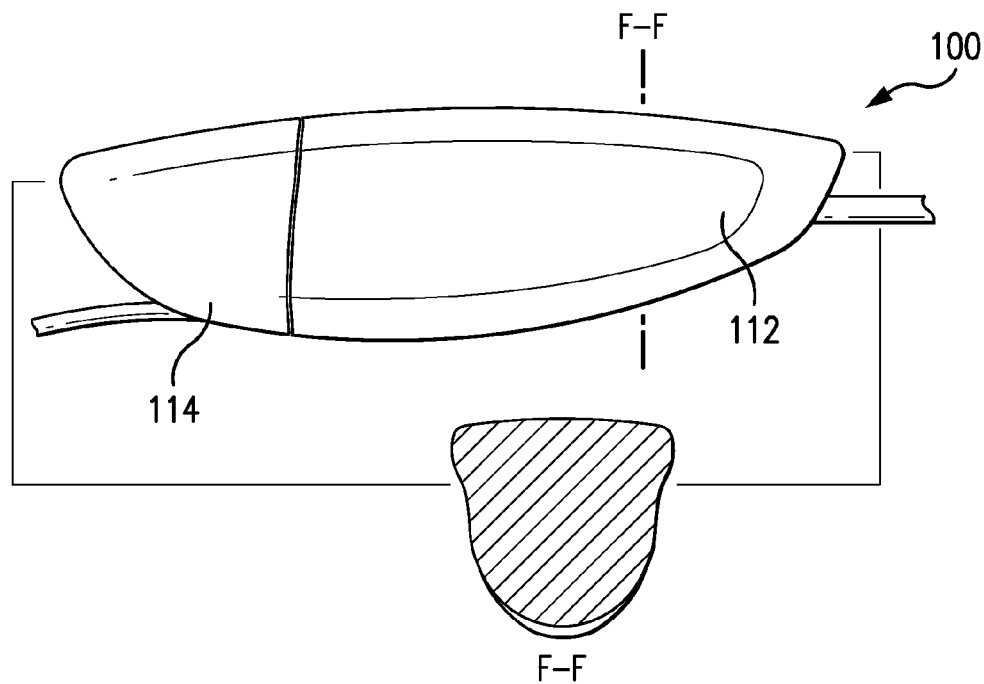
Figure 5Q:
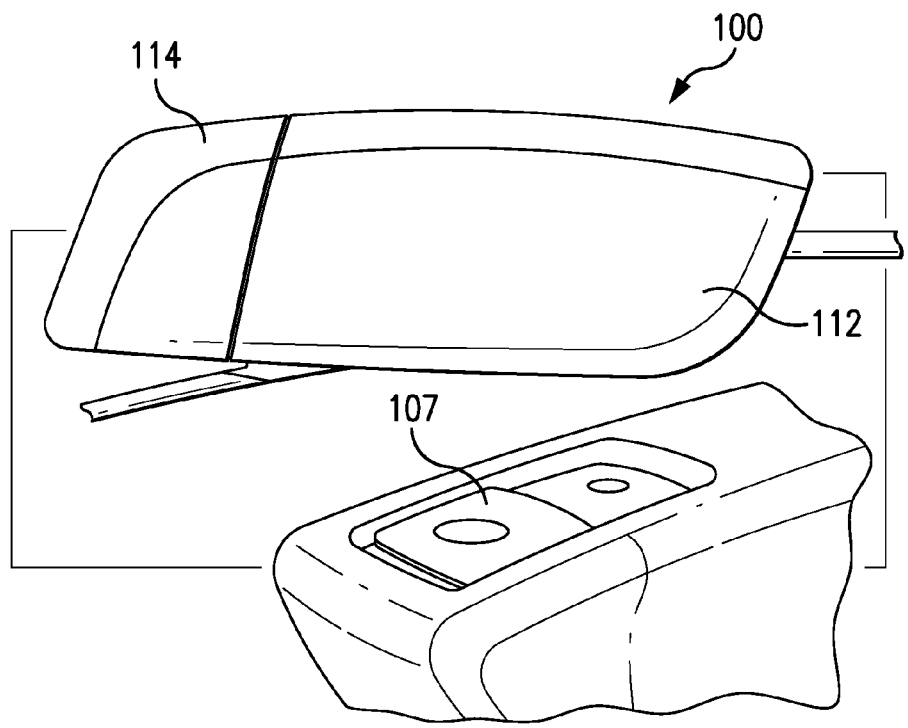
Figure 5R:
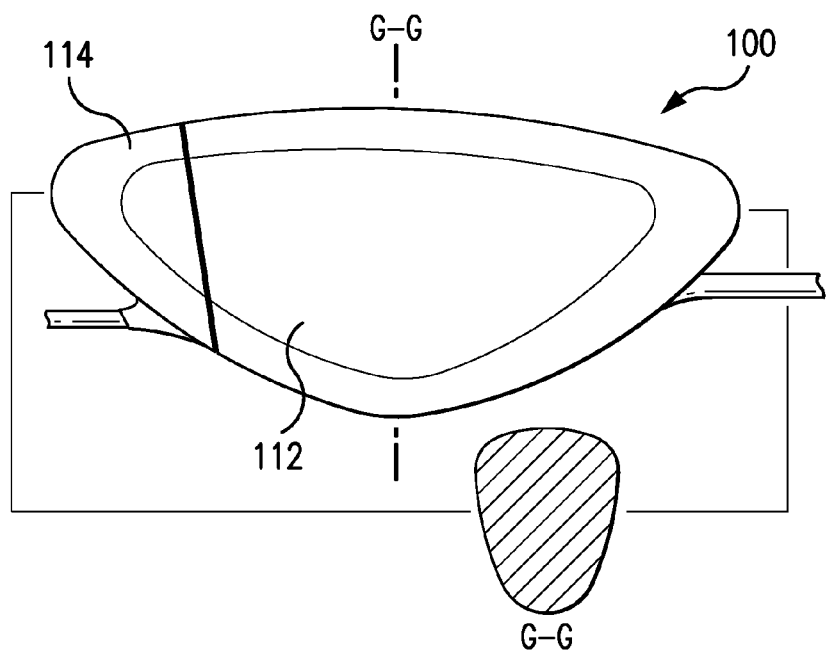

As described above, the catheter system includes a handle 100 generally disposed at or near the proximal end of the catheter. Handle 110 can include a housing of various shapes and configurations, as shown in FIGS. 5C to 5R. In one embodiment, handle 100 is non-removably attached to the catheter such that the system is a unitary device requiring assembly prior to use. In other words, the catheter system can be sold in a "ready-to-use" state, unlike conventional angioplasty catheters as described above.

The fluid circuit generally includes the inflation and independent deflation lumen disposed along the catheter shaft 200, a control system disposed in the handle 100 and a plurality of valves to control and regulate pulsated and/or modulated flow of inflation fluid through the catheter system.

In some embodiments, elongate shaft 200 includes an inlet port and an outlet port. The inlet port is pressurized by a flow of inflation fluid from a first reservoir as part of the control system 1000 of the fluid circuit. The inflation fluid flows through inflation lumen 203 of elongate shaft 200, enters the interior portion of the expandable member 300 via an inlet port. The inflow of the inflation fluid into the interior of expandable member 300 causes it to inflate and occlude the blood flow in the artery when disposed therein. An outlet port disposed on the elongate shaft 200 facilitates deflation of expandable member 300 by providing an opening for the inflation fluid to flow from expandable member 300 to deflation lumen 204 during deflation.

The outlet port is configured to facilitate Venturi-assisted flow in deflation lumen 204 to deflate expandable member 300. For example, inflation lumen 203 and deflation lumen 204 can both be open within expandable member 300. The inflation fluid can pass from inflation lumen 203, through expandable member 300, into deflation lumen 204. Inflation lumen 203 and the deflation lumen 204 are connected by a series of one-way check valves. In one embodiment, the inflation pressure causes the deflation check valve to stay closed. The pressure buildup (FIG. 7; 117, 112, and 109) on the back side of the check valve and pulse valve create a Venturi effect to promote rapid deflation. When the actuator is manipulated to the deflate position, pressure on the back side of a deflation check valve is removed. Thus the check valve opens and expandable member 300 can deflate. The rapid exhaustion of the inflation pressure creates a Venturi effect, i.e. it draws the balloon down, and pulls the inflation fluid along. Thus, in some embodiments, the expandable member is deflated in less than one second, and in some embodiments, less than ¼ of a second.

In one embodiment, as depicted in FIG. 5A, the control system 1000 includes an actuator 107 that is capable of actuating inflation and deflation of expandable member 300 with the ease of a flip of a finger. Actuator 107 can be actuated to sequentially inflate and deflate a balloon for post-conditioning applications or other applications. It has been found that reperfusion injury can result from rapid opening of an artery after a period of ischemia or interrupted blood flow, as for example but not limitation during a STEMI or other occlusion. One method for decreasing reperfusion injury is to sequentially start and stop the blood flow in the infracted artery for multiple cycles immediately after reopening the initial flow from the STEMI or other blockage. The present disclosure provides physicians with a system designed to achieve efficient, rapid, reproducible post-conditioning. Fluid circuit 110, including control system 1000, is designed to allow operation of the system by a single actuator 107 with no other input or electronics required referred to as "one-touch." Actuator 107 can be configured to include a first position or direction for inflation and a second position or direction for deflation of expandable member 300. For example, the actuator 107 can be a button (FIG. 5F), a switch (FIG. 5A), or a lever (FIG. 5B), having a momentary direction to actuate inflation and a detentable direction to actuate deflation of the balloon. By limiting physician interaction to only one switch, button, or lever, reproducibility in inflating and deflating expandable member 300 in accordance with the time requirements required for post-conditioning can be provided. Accordingly, the fluid circuit design and one-touch actuation provides ease of use for post-conditioning, and provides a high degree of reproducibility. Additionally, the device embodied herein allows the physician administering post-conditioning to focus on the monitor or other instrumentation, as opposed to necessarily focusing on the device during use.

In one embodiment, the inflation fluid is released from the reservoir 101 to regulator or a single pressure check valve, which controls the fluid pressure to the balloon 300. The regulated inflation fluid flows through an inlet tubing 106 to the actuator 107, (e.g., switch) which controls the flow of inflation fluid to the pulse valve 113 through a check valve and then to balloon 115.

Figure 6A:
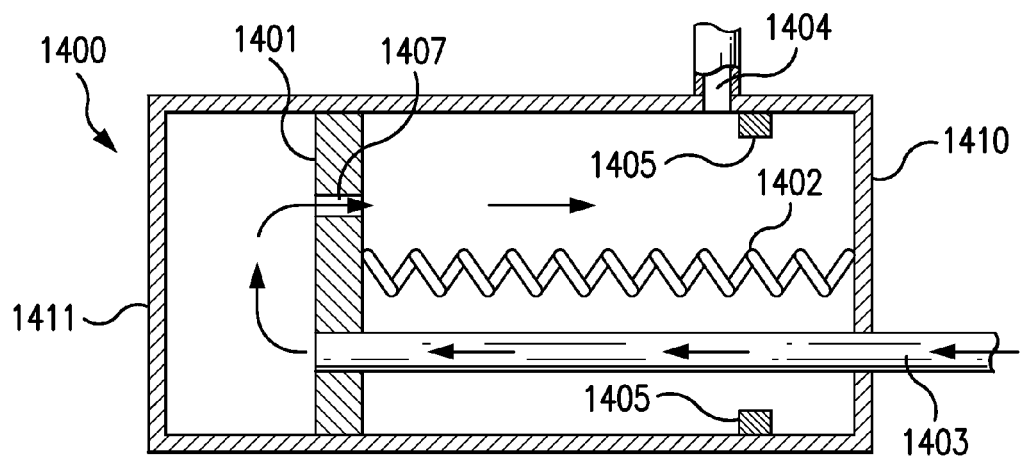
FIGS. 6A to 6C are schematic illustrates of a pulse valve in accordance with the disclosed subject matter.
Figure 6B:
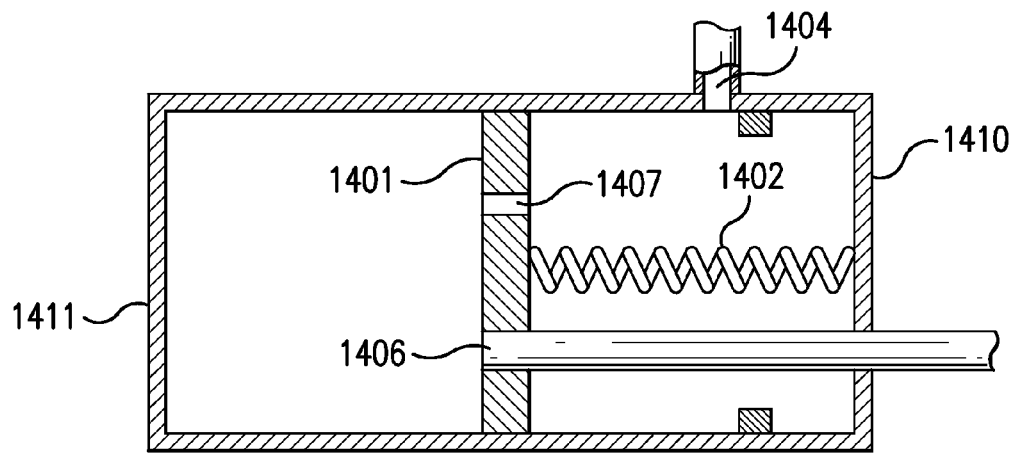
Figure 6C:
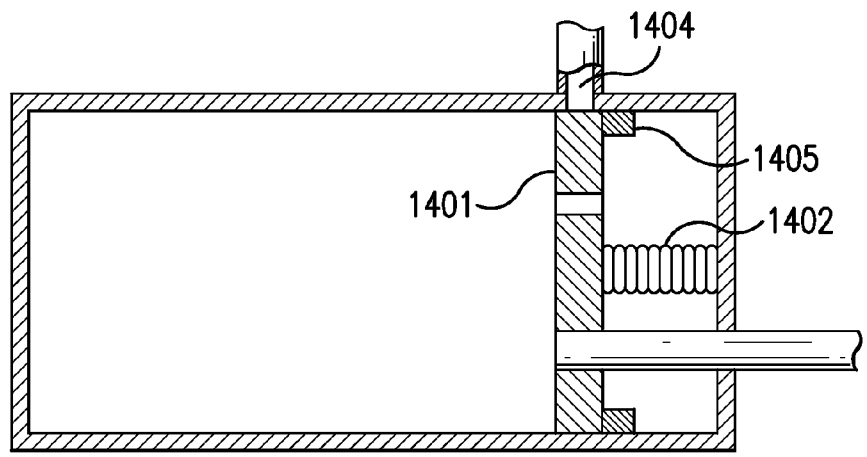

The pulse valve 113 allows inflation fluid to flow from an inlet port to an outlet port within the valve for a specified period of time. The time can be specified, for example, by sizing the inlet port, outlet port, and opposing spring pressure inside the pulse valve, as described below. As best shown in FIGS. 6A to 6C, in one embodiment, the pulse valve 113 includes an inner wall 1401 disposed within cylindrical body 1400. Cylindrical body 1400 has a first end 1410 and opposing second end 1411. An inner wall 1401 having an inlet port 1406 and an outlet port 1407 is disposed within the body 1400 between first and second ends 1410 and 1411. Preferably, the inlet port 1406 is larger than the outlet port 1407 such that inflation fluid flows through the inlet port into the cylindrical body between the second end 1411 and inner wall 1401 at a faster rate than that which flows through the outlet port 1407 to the cylindrical body between the first wall 1410 and inner wall 1401. Accordingly, the amount of inflation fluid entering the inlet port 1406 compared to the amount of inflation fluid exiting the outlet port 1406 causes a buildup of fluid pressure between second wall 1411 and inner wall 1401. The buildup of pressure consequently applies a force to the inner wall and eventually overcomes the strength of spring 1402 and causes the spring to compress, as shown in FIG. 6B as the inner wall is pushed from the pressure buildup. The inner wall 1401 contacts a stop member 1405 disposed within the cylindrical body 1400. In some embodiments a stop is provided on the inner surface of the cylindrical body. The stop is disposed proximate to an outlet port 115 which leads to a pathway to expandable member, e.g., balloon 300 (not shown). As shown in FIG. 6C, the inner wall 1401 contacts stop 1405 and becomes axially aligned with outlet port 115 to balloon 300. When inner wall 1401 is axially aligned with outlet port 115, the passageway provided by the port is blocked so that no inflation fluid can travel to the expandable member 300. Accordingly, the pulse valve 113 provides a "fool-proof" actuator. In this regard, the physician even if continually depressing the actuator to inflate the expandable member 300, cannot further inflate the expandable member because the outlet 115 is blocked by the inner wall 1401. Thus even if additional attempts at inflation are made, the system must de-energize before more inflation fluid is enabled to pass through the system. Thus, the system can safely control the amount of fluid entering an expandable member. The inflation fluid can be various fluids known in the art. For example, the inflation fluid can be a gas fluid or a liquid fluid. For the purpose of illustration, the inflation fluid can be carbon dioxide or saline.

In another embodiment, the fluid circuit includes a Venturi-assisted deflation of the expandable member. In this manner, a vacuum is created to rapidly deflate the inflation fluid from the expandable member. In this regard, when deflation is actuated by the physician, the pulse valve is de-energized, the fluid inside the pulse valve escapes thus relieving the pressure on the back side of a check valve, which creates a Venturi effect that decreases the time to deflate the balloon. In some embodiments, the expandable member deflates in less than about 5 seconds, preferably in less than about 3 seconds.

Figure 7:
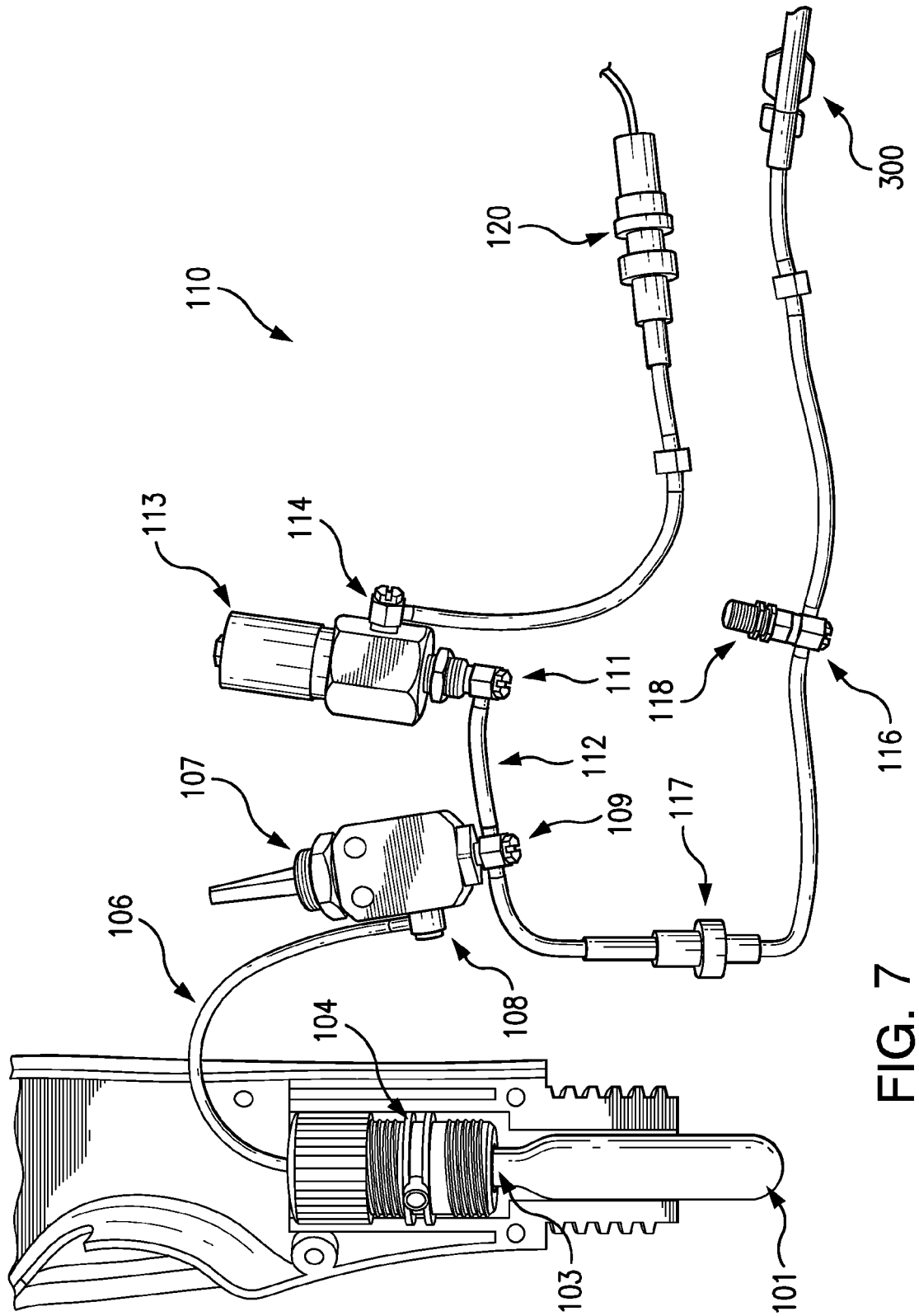
FIG. 7 is an exploded view of fluid circuit in accordance with one embodiment of the disclosed subject matter.
Figure 7E:
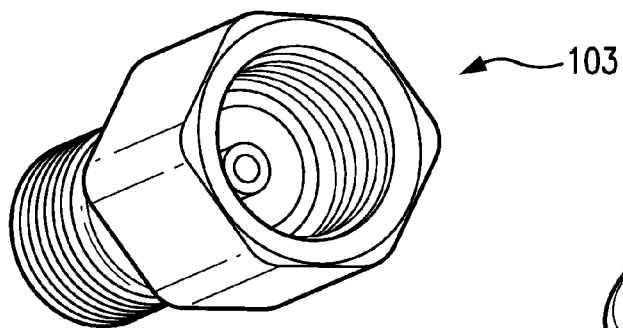
FIGS. 7A to 7T are perspective views of exemplary components of the fluid circuit of FIG. 7.
Figure 7F:
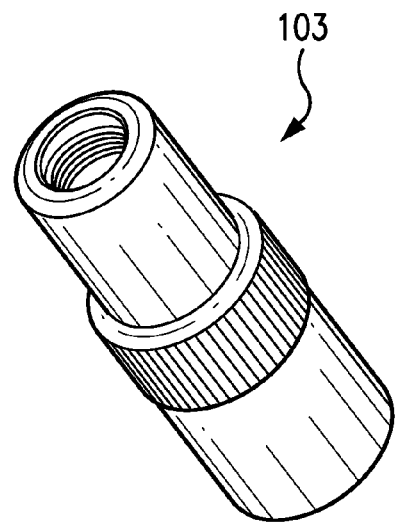
Figure 7G:
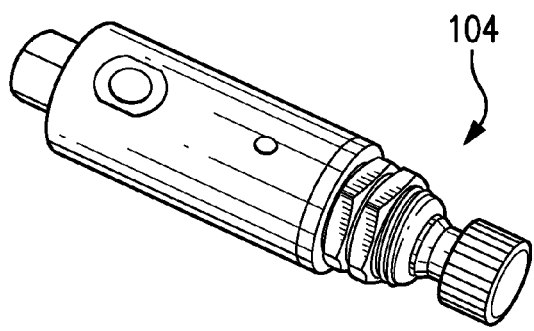
Figure 7H:
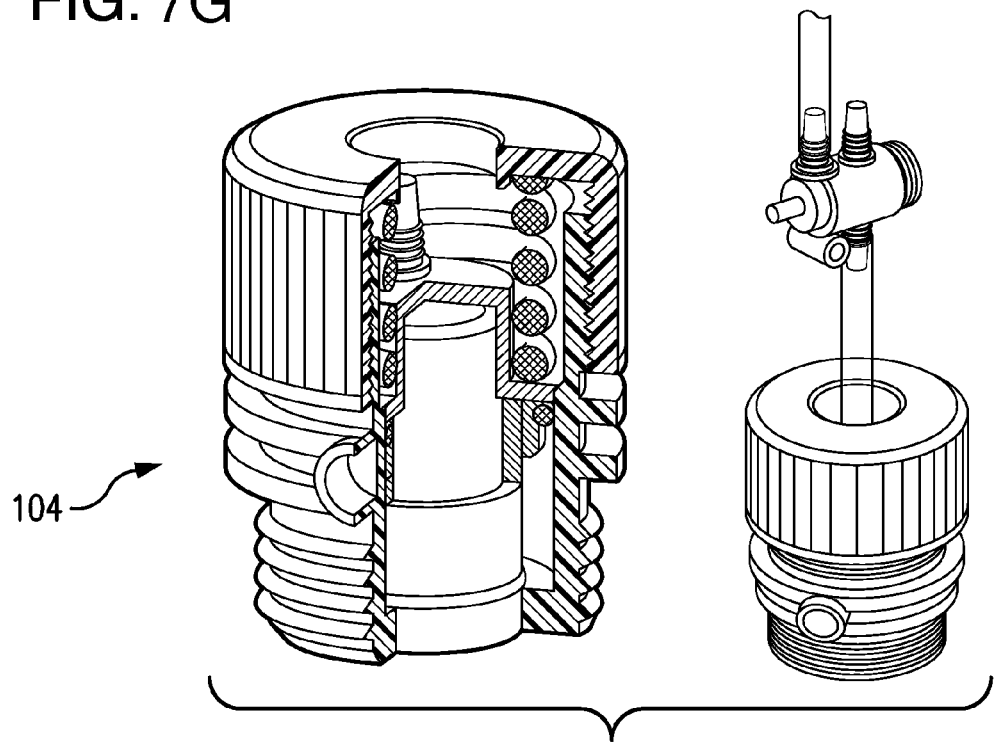
Figure 7I:
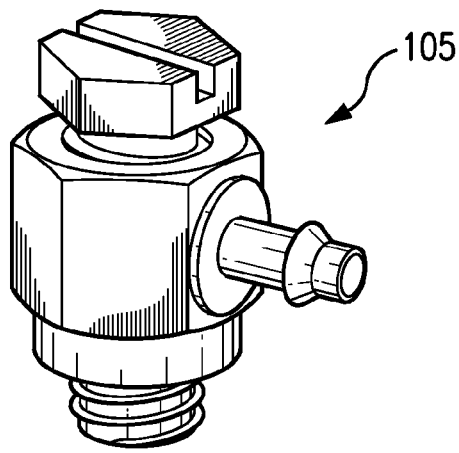
Figure 7J:
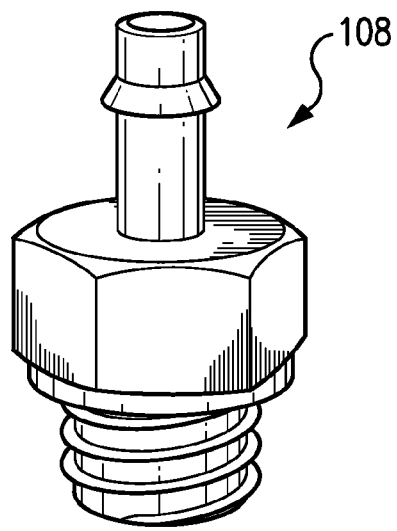
Figure 7K:
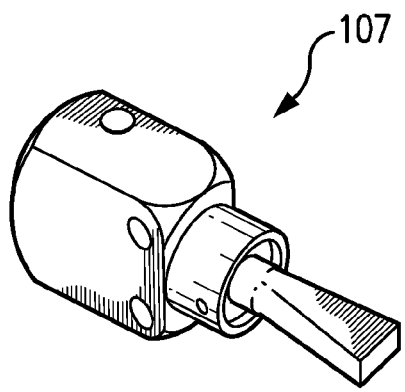
Figure 7L:
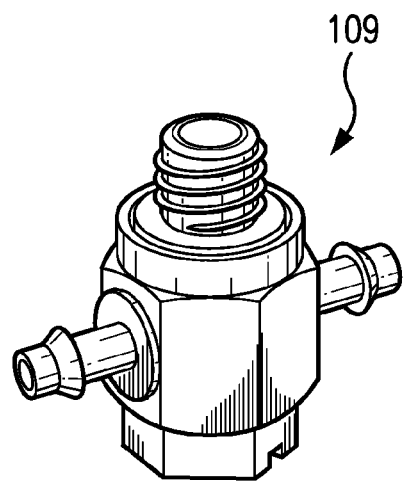
Figure 7M:
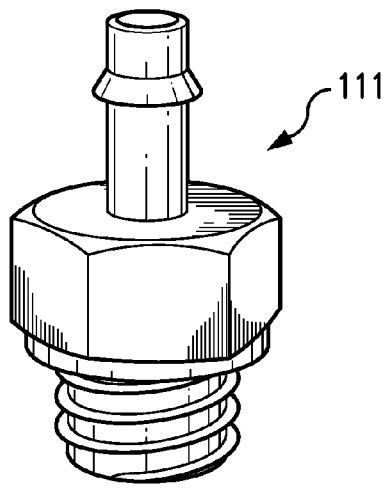
Figure 7N:
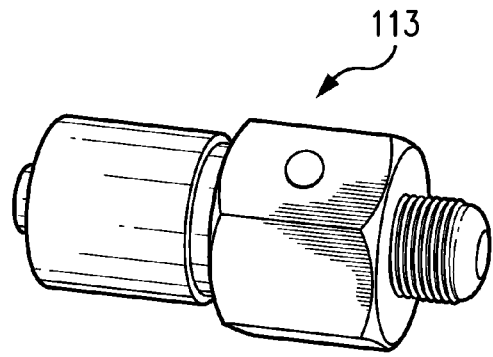
Figure 7O:
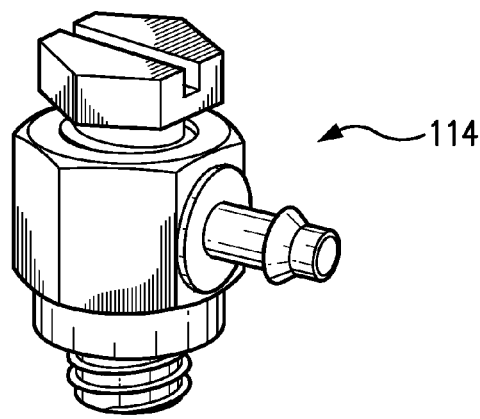
Figure 7P:
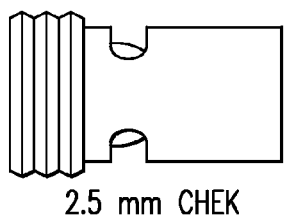
Figure 7P:
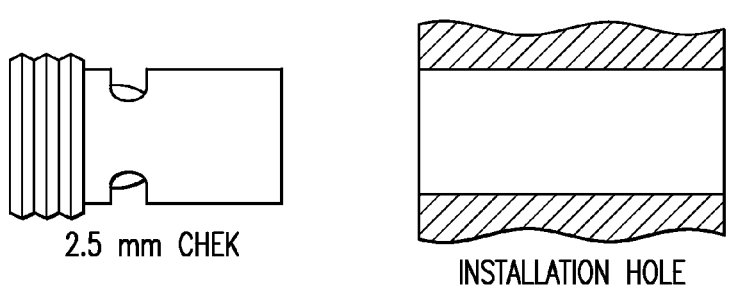
Figure 7P:
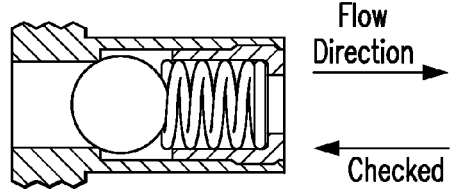
Figure 7P:
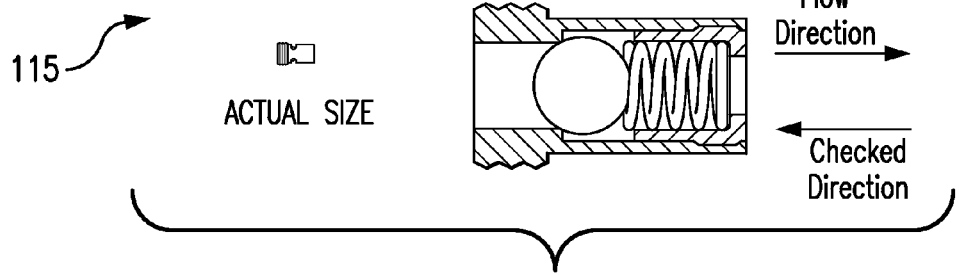
Figure 7Q:
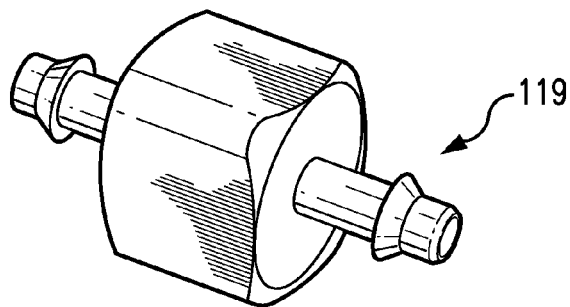
Figure 7R:
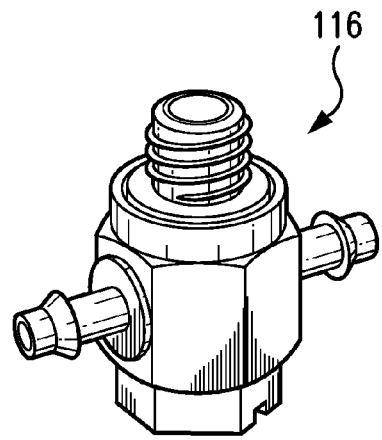
Figure 7S:
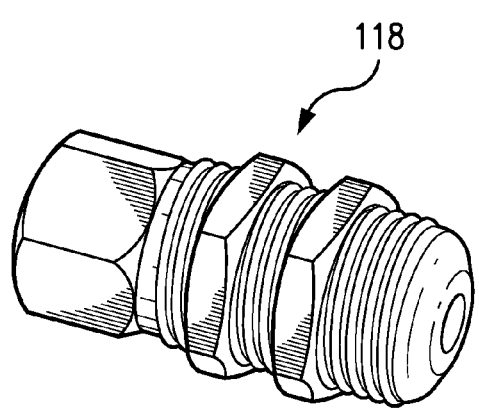
Figure 7T:
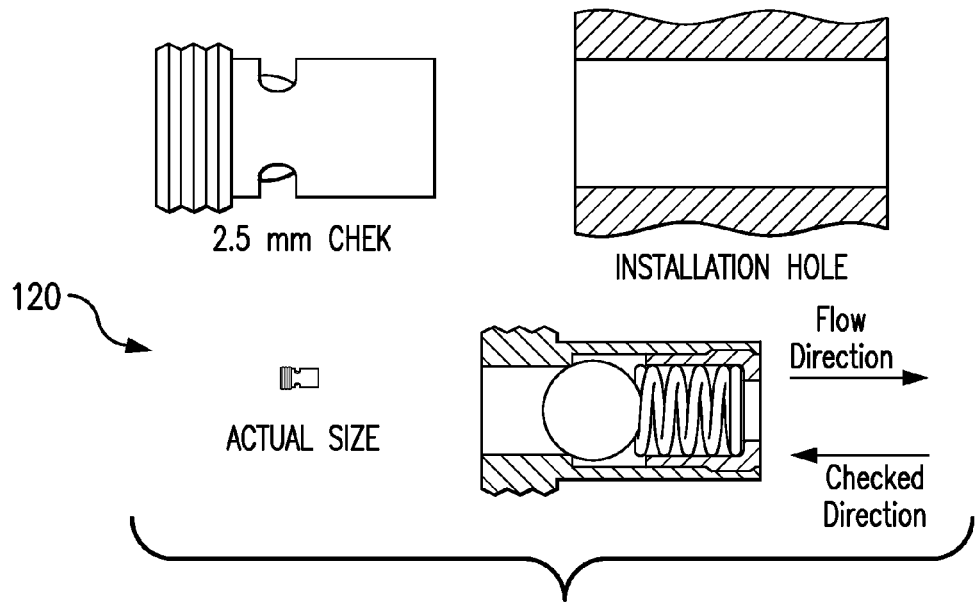

As described herein, the fluid circuit 110 generally includes tubing 106 and a plurality of check valves to modulate flow of the inflation fluid through the fluid circuit and eventually to the inflation lumen of elongate shaft 200, which is in communication with fluid circuit 110 and expandable member 300 and back through an independent deflation lumen. An exploded view of one embodiment of the fluid circuit is illustrated in FIG. 7. Fluid circuit 110 housed in the handle 100, can include the following component parts: first reservoir 101 to provide high pressure inflation fluid, such as but not limited to a BestWhip (LG) (Genuine Innovations, Part 2042 or 4130) (FIG. 7A); a piercing mechanism 103 to controllably tap the first reservoir 101, such as lance assembly, e.g., SA00102, SA00068, SA00101, or MM235008-21N, MM235008-11N (Genuine Innovations) (FIGS. 7B-7F, respectively); pressure regulator 104 (e.g., MAR-1 (Clippard) or SA00196 (Genuine Innovations), FIGS. 7G-7H, respectively) to control pressure from inflation fluid to expandable member 300. Alternatively, a single pressure check valve or a non-variable pressure regulator can be used such as for example, Qosina—P/N 11582 or "Lee Chek" Part Number CCPI2510014S, (FIG. 7P); connector 105 (not shown) to connect the pressure regulator 104 to tubular member 106, e.g., UTO-2-PKG (Clippard) (FIG. 7I); actuator 107 to control the flow of inflation fluid from first reservoir 101 into expandable member 300; e.g., a main switch such as FBV-3DMF (Clippard) (FIG. 7K); connector 108 to connect tubular member 106 from pressure regulator 104 to actuator 107, e.g., CT2-PKG (Clippard) (FIG. 7J); flow splitter 109 to split the flow of inflation fluid, e.g., UT0-2002-PKG (Clippard) (FIG. 7L); connector 111, such as, e.g., the CT2-PKG (Clippard) (FIG. 7M), to connect flow splitter 109 to pulse valve 113, such as, e.g., PV-1 (Clippard) (FIG. 7N), through tubular member 112 to deliver a volume of controlled pulse of inflation fluid to expandable member 300; a connector 114, such as a rotational connector, e.g., UTO-2-PKG (Clippard) (FIG. 7O), to connect pulse valve 113 to a one-way check valve 115 (e.g., CCPI2510000S (Lee Company) or Qosina—P/N 11582 (FIG. 7P) that permits flow of inflation fluid to expandable member and ensures the flow direction of the inflation fluid is one-way only, i.e., from pulse valve 113 to inflation lumen 203 of elongate shaft 200; flow splitter 116, such as, e.g., UT0-2002-PKG (Clippard) (FIG. 7R) which is connected to flow splitter 109 through tubular member 117, wherein flow splitter 109 connects the hose from deflation lumen 204 to pressure indicator 118; pressure indicator 118, such as, e.g., IND-1-WH (Clippard) (FIG. 7S), for showing that there is pressure in deflation lumen 204 to ensure expandable member 200 is inflated; double hose barb 119 (not shown), such as C22-PKG (Clippard) (FIG. 7Q), for connecting check valve 120 to the hose going to the catheter; and check valve 120, such as CCPI12510000S (Lee Company) (FIG. 7T), to ensure the flow direction of inflation fluid from the outlet lumen on the catheter pulse valve to inlet lumen 203.

Figure 8A:
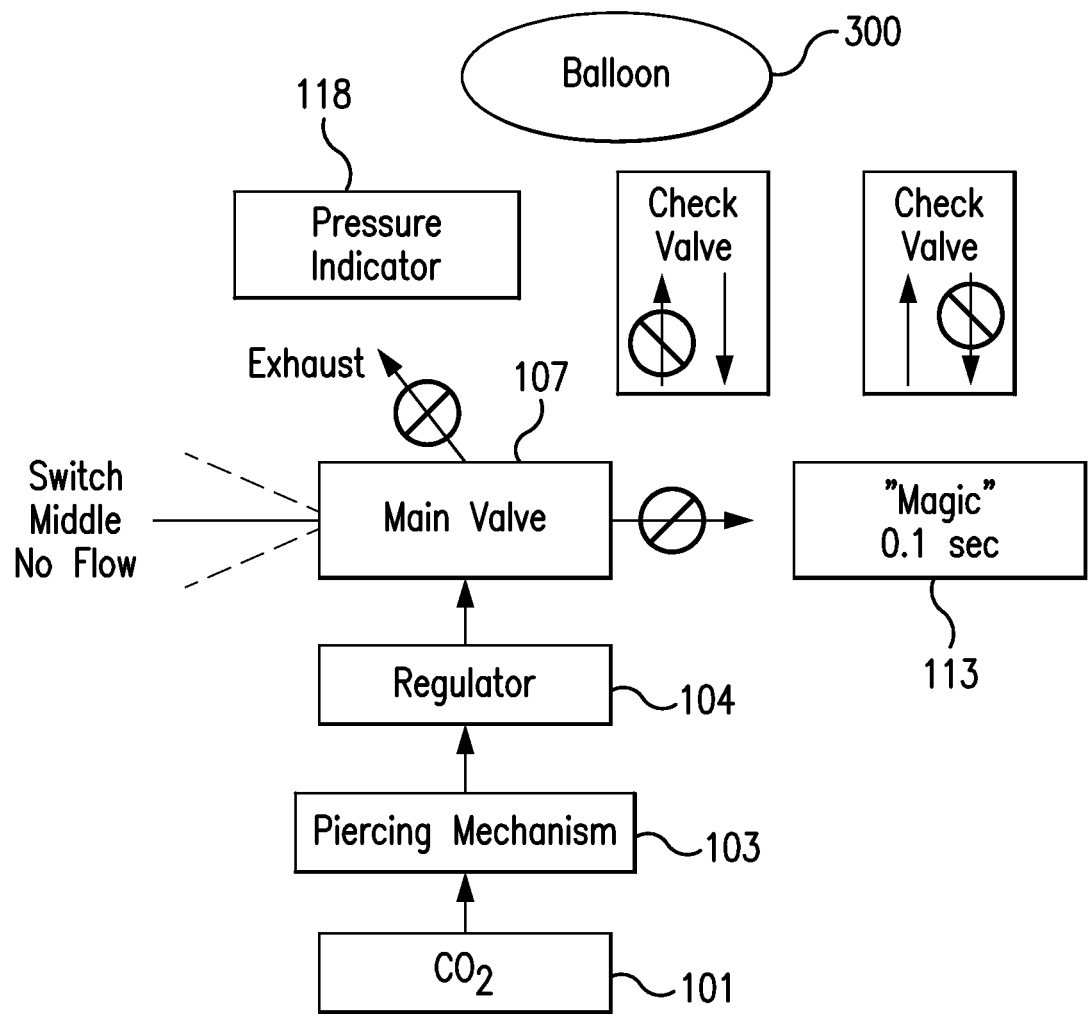
FIGS. 8A to 8C are block diagrams illustrating the inflation fluid flow through the fluid circuit in accordance with one embodiment of the disclosed subject matter.
Figure 8B:
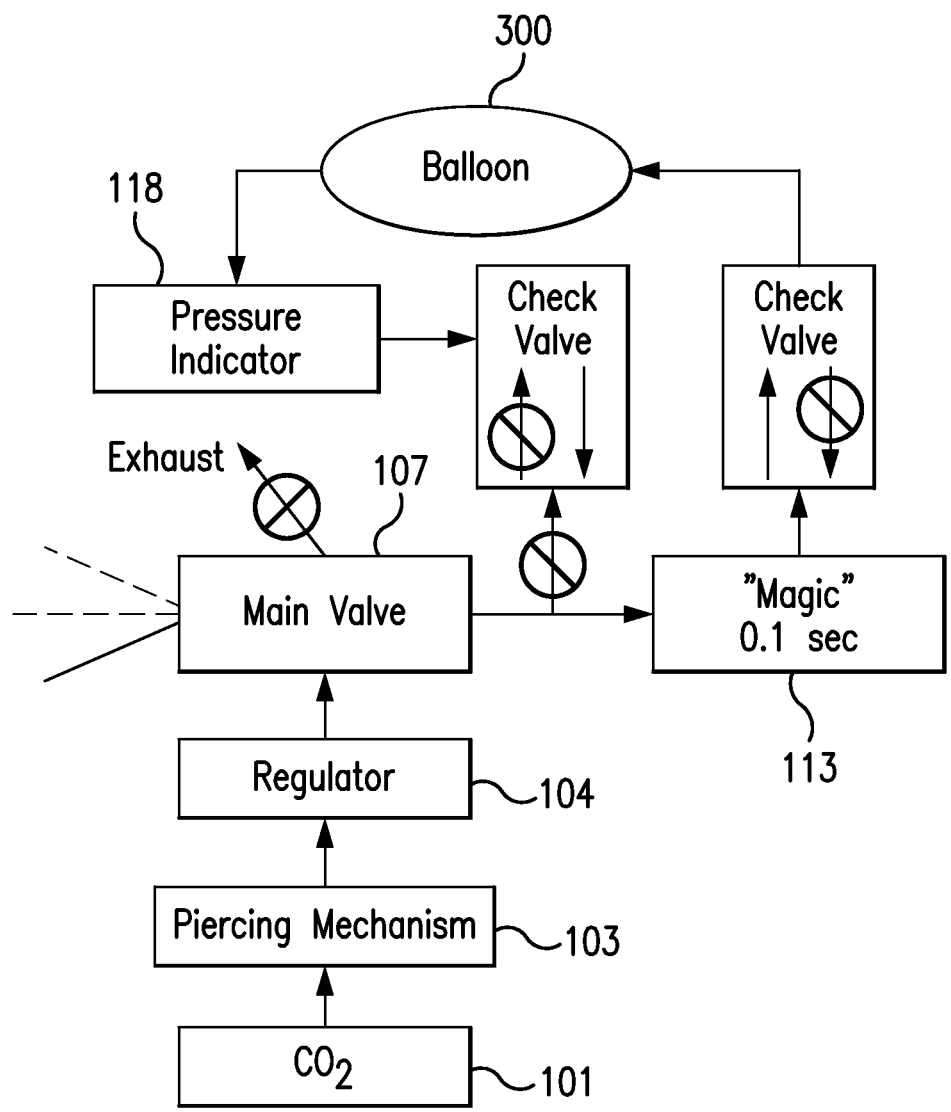
Figure 8C:
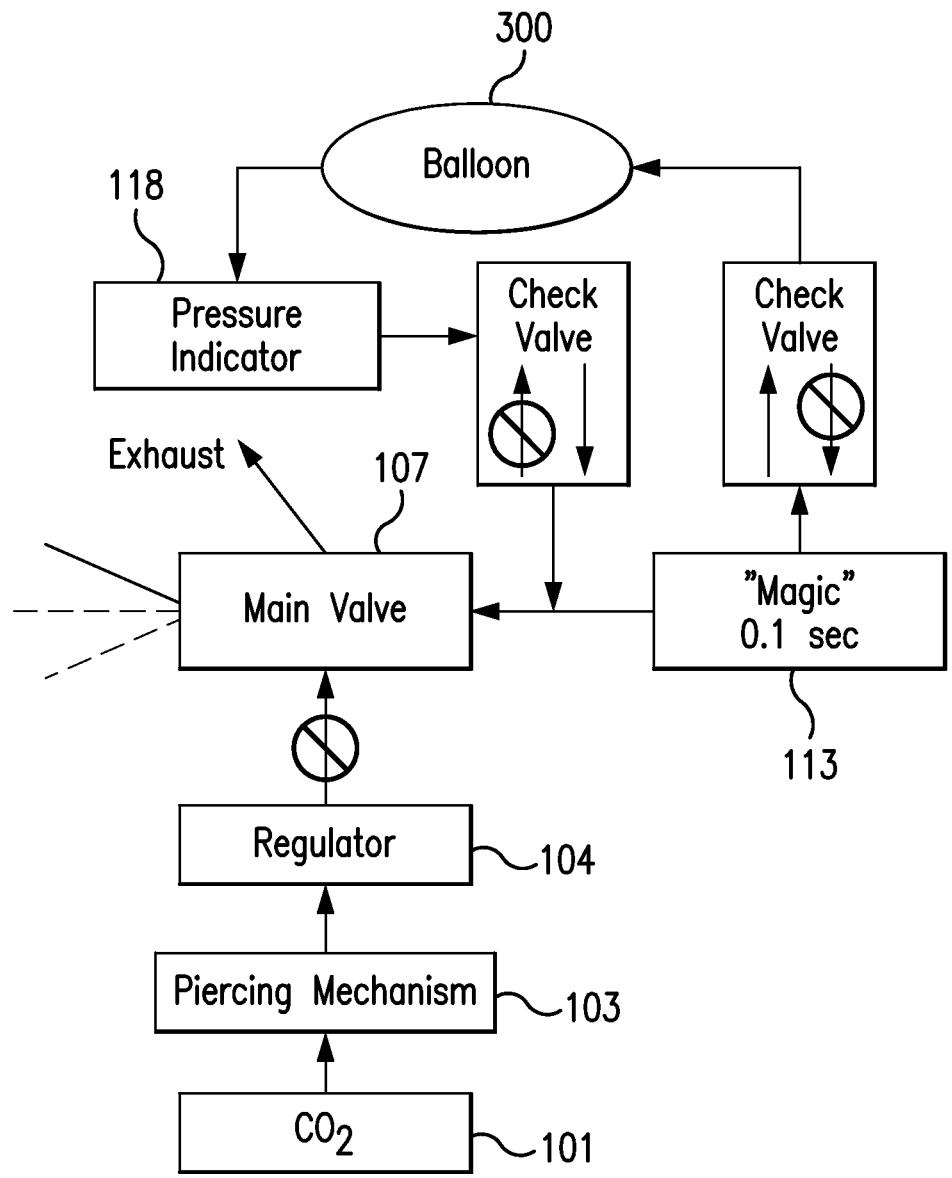

As illustrated in the block diagram of FIG. 8A, in operation the inflation fluid, in this example carbon dioxide, flows out from storage in the first reservoir 101 by a piercing mechanism 103. The inflation fluid flows into a main valve or actuator switch. In some embodiments, the flow of inflation fluid is stopped into and out of the main valve. As shown in FIG. 8B, the fluid circuit can be configured to allow the inflation fluid to flow across the valve into a second check valve. The gas is allowed to flow, in some embodiments, for about 0.1 seconds. After that time, the second valve can be configured to no longer allow flow of the inflation fluid. The check valve allows flow of the inflation fluid into the balloon but not out of the balloon. A third check valve allows inflation fluid flow out of the balloon, but not into the balloon. The inflation fluid, such as the carbon dioxide gas, has a higher pressure when it flows to the inflation check valve, so the system is locked (inflated) at this time. Further, as depicted in FIG. 8C, the pressure inside the second valve exhausts, thereby creating a Venturi force, as noted above, which pulls the balloon into a deflated position as all the gas exhausts out from the top of the main valve. The main valve does not allow gas to flow in at this time. Accordingly, the fluid circuit permits the user to sequentially inflate and deflate the expandable member with the ease of rapid succession. The handle may further include a pulse valve to deliver time-controlled, or volume-controlled flow to the balloon 300. In this regard, the second tubular member may include a one-way check valve to lock the pulse valve delivered carbon dioxide in the expandable member 300.

V. Indicator

Deflation lumen, in some embodiments, includes an indicator, such as but not limited to a pressure monitor, which ensures balloon is inflated. In some embodiments the pressure monitor is disposed in-between the balloon and a deflation check valve to ensure the balloon is inflated. For example, if the catheter is kinked and not allowing inflation, then the indicator will not indicate inflated. Additionally, if the catheter has a leak at the balloon, then the indicator will not indicate inflated. Accordingly, the indicator is a true test of balloon inflation.

In one embodiment, the indicator 118 (FIGS. 5A, 7) or a pressure marker is disposed at a proximal end of the system. In one embodiment, the indicator 118 includes a projection member associated with the deflation lumen of the system. In some embodiments, the indicator 118 is configured to extend at least partially through handle 100 when pressure is sensed in the deflation lumen of the system. In this manner, the indicator orientation can inform the physician of the state of the expandable member. In other words, when the indicator extends from the handle housing 100 and is visible to the physician due to, for example, pressure, forcing the button to extend then the physician is cognizant of the fact that inflation fluid is in the expandable member. Conversely, non-extension of the indicator from the handle 100 informs the user that the expandable member is not fully inflated. As the indicator is in associated, such as for example, coupled, to the deflation lumen at the proximal end of the system, the indicator cannot indicate or extend until pressure from the inflation fluid has flowed through the inflation lumen, made fluid communication with the expandable member, and returned through the deflation lumen to the proximal section of the system. Thus, indicator 118 cannot indicate pressure unless the expandable member is inflated at the distal section of the catheter system. Advantageously, the indicator is an indication of the true pressure inside the balloon. Conversely, an indicator which is not in direct fluid communication with a deflation lumen will not truly indicate if the balloon is inflated or deflated.

VI. Arming the Device

In one embodiment, as shown in the cross sectional views of FIGS. 5A and 5B and best seen in FIG. 7, the control system 1000 of fluid circuit 110 generally includes a first reservoir 101, such as a container or canister, having stored inflation fluid. The first reservoir 101 can be selected (based on size) to inflate and deflate particular balloons of specified sizes. Accordingly, the size of the reservoir selected can prevent reuse and/or promote safety, especially when the inflation fluid is a pressurized gas such as carbon dioxide.

Figure 9C:
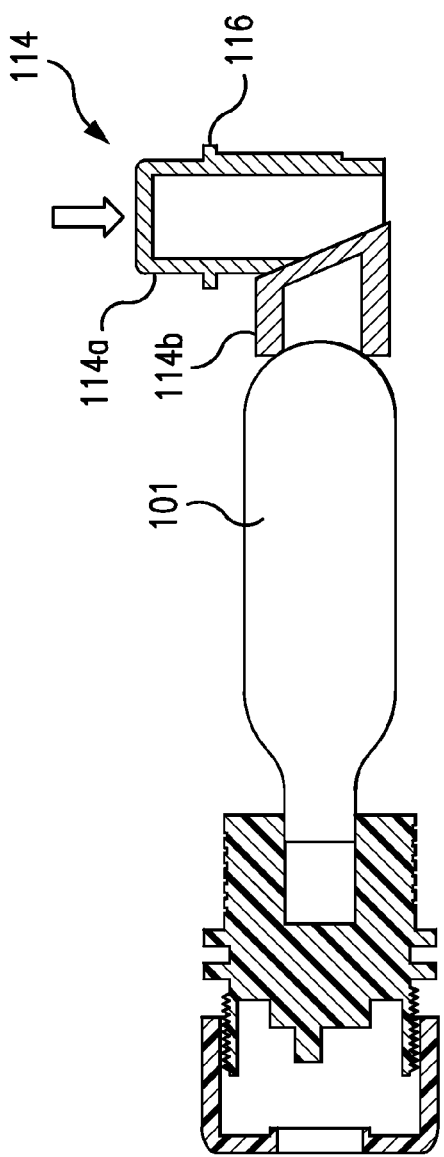
FIGS. 9A to 9N are side views of some embodiments of an arming device in accordance with the disclosed subject matter.
Figure 9D:
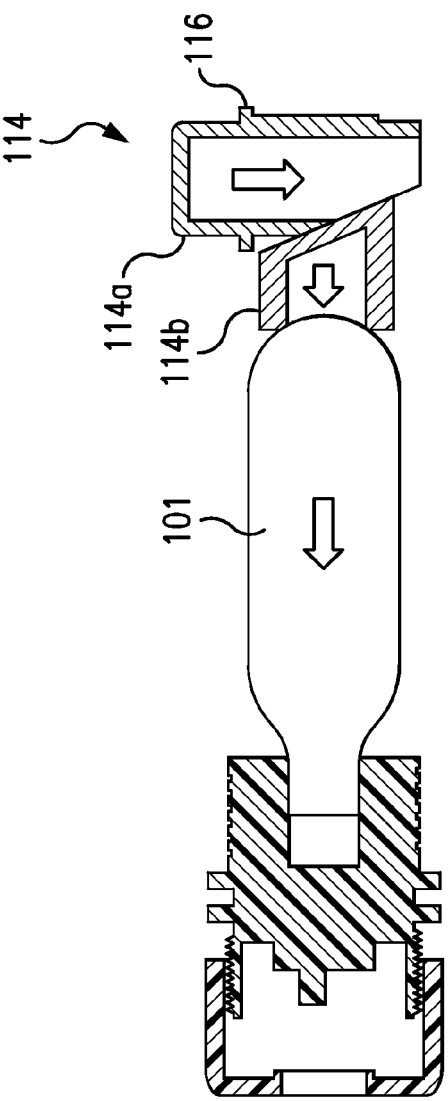
Figure 9I:
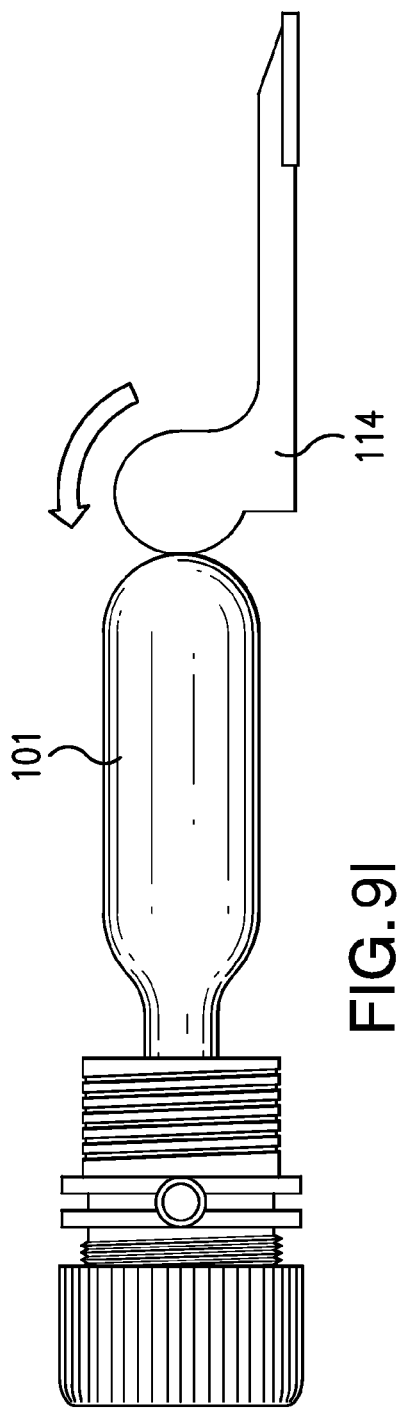
Figure 9J:
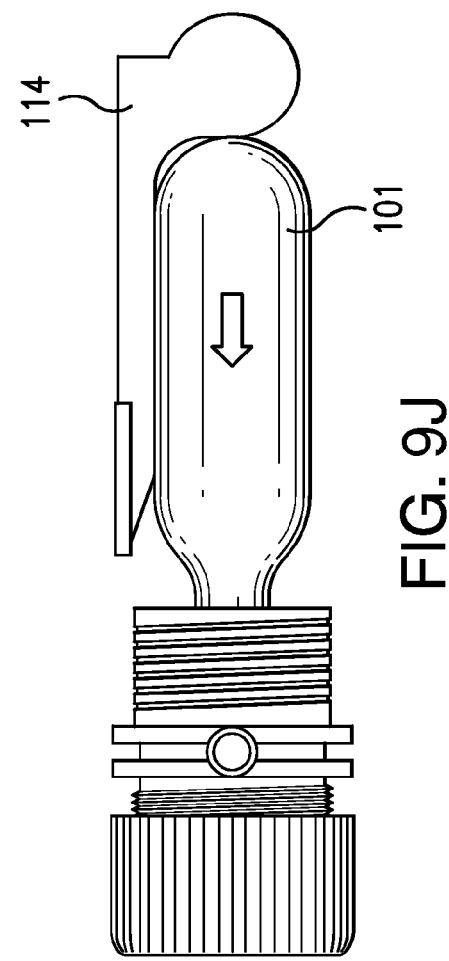

In some embodiments, an arming device 114 (FIG. 9A) is disposed proximal to the first reservoir and is configured to arm the device. The arming device can be non-reversible. In this regard, "non-reversible" means that once the device is armed, it cannot be disarmed. The arming device 114 is actuated by the physician prior to use in order to pierce the reservoir 110 which contains the inflation fluid. For example, as depicted in FIGS. 9A and 9B, when arming device 114 is pushed down, first reservoir 101 is pushed forward and a ratchet located on handle housing 112 engages tab 116, thus preventing arming device 114 from returning to its original position. The system is armed, thereby allowing the fluid to flow from an opening in first reservoir 101.

Further embodiments of arming device 114 are depicted in FIGS. 9C-9N. For example, in FIGS. 6C and 6D, arming device 114 is formed from button 114a and wedge 114b which are positioned such that a downward force on button 114a causes wedge 114b to move in a perpendicular direction, thereby advancing first reservoir 101 forward into an armed position by releasing inflation fluid stored in the reservoir 101. Tab 116 again engages a ratchet located on handle housing 112, preventing both button 114a and wedge 114b from returning to their original positions.

Lever type safeties 114 are depicted in FIGS. 9E to 9J. As shown, the physician must move the lever from a first position to a second position in order to advance first reservoir 101 into its armed position. The initial and final position of lever arming device 114 depend solely on the manufacturing requirements of the system. In some embodiments, a ratchet located on the side of handle housing 112 engages the sides of lever arming device 114, thereby preventing lever arming device 114 from returning to its original position.

A pull tab type arming device 114, as shown in FIGS. 9K-9L, may also be utilized in accordance with some embodiments of the invention. In such embodiments, pull tab type arming device may be formed from pull tab 114c and spring mechanism 114d. The spring is biased in a contracted state until the pull tab is removed. By removing pull tab 114c from handle 100, spring mechanism 114d is allowed to expand such that the spring applies a force that pushes or otherwise allows first reservoir 101 to engage a tapping device such as a lancet to arm the device.

In other embodiments, arming device 114 may be a screw type arming device, as depicted in FIGS. 9M-9N. As shown, threads 114e, located on arming device 114, engage an opening in housing 112. Rotating arming device 114 in the appropriate direction causes arming device 114 to advance forward and advance first reservoir 101 into its armed position. In some embodiments, arming device 114 may contain a locking mechanism (not shown) that prevents first reservoir 101 from being disarmed and/or rotating in the wrong direction.

As described the arming device 114 arms the first reservoir 101 by causing engagement of the first reservoir 101 with piercing member 103 (FIGS. 5B, 7) so that the reservoir is tapped or pierced to release the inflation fluid contained in the reservoir housing. The outflow of inflation fluid enters the fluid circuit and eventually flows to the expandable member at the distal section of the catheter body and out from the balloon via an independent deflation lumen.

What is claimed is:

1. A catheter system comprising:
   a single balloon;
   a catheter shaft including an inflation lumen and an independent deflation lumen disposed between a proximal section and a distal section of the shaft, wherein the inflation lumen and the deflation lumen are both in fluid communication with the single balloon, and
   an indicator associated with the deflation lumen, wherein the indicator indicates inflation of the balloon.

2. The catheter system of claim 1, wherein the catheter is useful in reducing or preventing reperfusion or retroperfusion injury.

3. The catheter system of claim 1, wherein the balloon is a compliant balloon.

4. The catheter system of claim 1, wherein the balloon has a length less than about 10 mm.

5. The catheter system of claim 1, wherein the balloon has a length of about 6 mm.

6. The catheter system of claim 3, wherein the compliant balloon is capable of molding to the shape of a blood vessel when disposed and inflated therein.

7. The catheter system of claim 3, wherein the compliant balloon is configured to occlude a blood vessel when the balloon is inflated with less than about 1 atmosphere of pressure.

8. The catheter system of claim 7, wherein the compliant balloon is configured to occlude an eccentric blood vessel.

9. The catheter system of claim 1, wherein the balloon is configured to occlude a blood vessel having a diameter of about 2 to 4.5 mm.

10. The catheter system of claim 1, wherein the balloon is configured to occlude a blood vessel having a diameter of about 4 to 30 mm.

11. The catheter system of claim 1, wherein the balloon has a substantially spherical shape while inflated.

12. The catheter system of claim 2, wherein the balloon is a one-size-fits-all balloon.

13. The catheter system of claim 1, wherein the balloon is sequentially inflatable and deflatable.

14. The catheter system of claim 13, wherein the catheter is configured to inflate the balloon in about 5 seconds or less.

15. The catheter system of claim 13, wherein the catheter is configured to deflate the balloon in about five seconds or less.

16. The catheter system of claim 1, wherein the catheter exhibits Venturi-assisted deflation of the balloon.

17. The catheter system of claim 16, further including a pulse valve.

18. The catheter system of claim 17, wherein the pulse valve at least in part assists in creating a vacuum to assist deflation of the balloon.

19. The catheter system of claim 13, wherein the system is configured to deflate the balloon in about than 3 seconds or less.

20. The catheter system of claim 19, wherein the system is configured to deflate the balloon in less than 3 seconds.

21. The catheter system of claim 1, wherein the deflation lumen has a diameter larger than a diameter of the inflation lumen.

22. The catheter system of claim 21, wherein the diameter of the deflation lumen is about twice the size of the diameter of the inflation lumen.

23. The catheter system of claim 1, wherein the catheter further includes a guidewire lumen.

24. The catheter system of claim 23, wherein the guidewire lumen has a diameter larger than the deflation lumen.

25. The catheter system of claim 1, wherein the catheter further includes a drug delivery lumen.

26. The catheter system of claim 1, further including a drug delivery lumen and a guidewire lumen, and further wherein each of the lumen have a diameter size different than the other three lumen.

27. The catheter system of claim 1, wherein the catheter is a rapid exchange catheter.

28. The catheter system of claim 1, wherein the catheter is an over-the-wire catheter.

29. The catheter system of claim 2, wherein the reperfusion injury is an ischemia of a blood vessel of the cerebral, coronary, or peripheral vasculature.

30. A system for reducing or preventing reperfusion injury to a patient, the system comprising:
    a single balloon; and
    a catheter having a catheter shaft wherein the catheter shaft includes an inflation lumen and an independent deflation lumen, wherein the inflation lumen and the independent deflation lumen are both in fluid communication with the balloon;
    disposed on the catheter shaft, wherein the balloon is configured for sequential inflation and Venturi-assisted deflation.

31. The system of claim 30, wherein the balloon is deflated in less than about five seconds.

32. The system of claim 30, wherein the balloon is deflated in less than about three seconds.

33. The system of claim 30, wherein balloon is inflated in less than five seconds.

34. The system of claim 33, wherein a pulse valve is disposed between the inflation lumen and the deflation lumen.

35. The system of claim 34, wherein the pulse valve comprises a cylindrical body having first and second ends and an inner wall disposed between the first and second ends and a spring biased against the inner wall.

36. The system of claim 35, wherein the inner wall includes an inlet port and an outlet port and further wherein the inlet port is larger than the outlet port.

37. The system of claim 36, wherein inflation fluid enters the pulse valve, and further wherein the inflation fluid has a differential of fluid pressure is created in the cylindrical body.

38. The system of claim 37, wherein the pulse valve at least in part provides Venturi-assisted deflation of the balloon.

39. The system of claim 37, wherein the inner wall blocks an outlet port disposed on the cylindrical body of the pulse valve, and further wherein additional inflation fluid cannot flow into the balloon when the outlet port is blocked.

40. A system comprising:
    a single balloon;
    a catheter shaft including an inflation lumen and an independent deflation lumen, wherein the inflation lumen and the independent deflation lumen are both in fluid communication with the balloon;
    an indicator in communication with the deflation lumen; and
    an expandable member disposed on the catheter shaft, wherein the indicator is configured to notify a user of inflation or deflation of the expandable member.

41. The system of claim 40, wherein indicator is a balloon pressure marker.

42. The system of claim 41, wherein the balloon pressure marker indicates pressure in the deflation lumen.

43. The system of claim 42, wherein presence of fluid pressure in the deflation lumen indicates that the expandable member is inflated.

44. The system of claim 41, wherein the balloon pressure marker indicates when the expandable member is in a deflated state.

45. The catheter system of claim 1, further comprising a handle, wherein the indicator is associated with the handle.

46. The system of claim 40, further comprising a handle, wherein the indicator is associated with the handle.

* * * * *